United States Patent
Martinez-Castro et al.

(10) Patent No.: US 9,228,041 B2
(45) Date of Patent: Jan. 5, 2016

(54) COMPOSITIONS WITH PH RESPONSIVE COPOLYMER CONTAINING MAEP AND/OR MAHP AND METHOD FOR USING SAME

(71) Applicant: Rhodia Operations, Aubervilliers (FR)

(72) Inventors: Nemesio Martinez-Castro, Bristol, PA (US); Jennie McGuire, Lansdale, PA (US); Herve Adam, Clarksburg, NJ (US); James Woods, Wilmington, DE (US)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 14/132,685

(22) Filed: Dec. 18, 2013

(65) Prior Publication Data

US 2014/0178324 A1 Jun. 26, 2014

Related U.S. Application Data

(60) Provisional application No. 61/740,837, filed on Dec. 21, 2012.

(51) Int. Cl.

| | |
|---|---|
| *C08F 220/64* | (2006.01) |
| *C08F 220/18* | (2006.01) |
| *C07C 67/08* | (2006.01) |
| *C08L 33/08* | (2006.01) |
| *C09D 5/04* | (2006.01) |
| *C09K 8/68* | (2006.01) |
| *C11D 3/37* | (2006.01) |
| *C08F 20/06* | (2006.01) |
| *C08F 20/64* | (2006.01) |
| *C08F 220/06* | (2006.01) |
| *C08F 220/28* | (2006.01) |
| *C09K 8/588* | (2006.01) |
| *C09K 8/70* | (2006.01) |
| *C09K 8/74* | (2006.01) |
| *C11D 17/00* | (2006.01) |

(52) U.S. Cl.
CPC .............. *C08F 220/64* (2013.01); *C07C 67/08* (2013.01); *C08F 20/06* (2013.01); *C08F 20/64* (2013.01); *C08F 220/06* (2013.01); *C08F 220/18* (2013.01); *C08F 220/28* (2013.01); *C08L 33/08* (2013.01); *C09D 5/04* (2013.01); *C09K 8/588* (2013.01); *C09K 8/68* (2013.01); *C09K 8/685* (2013.01); *C09K 8/70* (2013.01); *C09K 8/74* (2013.01); *C11D 3/3757* (2013.01); *C11D 3/3765* (2013.01); *C11D 17/003* (2013.01); *C09K 2208/08* (2013.01)

(58) Field of Classification Search
CPC .......... C08F 20/02; C08F 20/04; C08F 20/06; C08F 20/28; C08F 20/64; C08F 220/02; C08F 220/04; C08F 220/06; C08F 220/28; C08F 220/282; C08F 220/64; C11D 3/3765; C11D 3/3757; C11D 17/003; C09K 8/70; C09K 8/588; C09K 8/685; C09K 8/68; C09K 2208/08; C07C 67/08; C08L 33/08
USPC .......................... 525/243, 301, 302, 308, 312
See application file for complete search history.

(56) References Cited

U.S. PATENT DOCUMENTS

| | | |
|---|---|---|
| 3,689,427 A | 9/1972 | Matsuda et al. |
| 3,779,970 A | 12/1973 | Evani |
| 3,937,283 A | 2/1976 | Blauer et al. |
| 4,384,096 A | 5/1983 | Sonnabend |
| 4,432,881 A | 2/1984 | Evani |
| 4,541,935 A | 9/1985 | Constien et al. |
| 4,569,965 A | 2/1986 | Engel et al. |
| 5,292,843 A | 3/1994 | Jenkins et al. |
| 5,374,687 A | 12/1994 | Cooperman et al. |
| 5,431,956 A | 7/1995 | Robb et al. |
| 5,510,306 A | 4/1996 | Murray |
| 5,551,516 A | 9/1996 | Norman et al. |
| 5,566,760 A | 10/1996 | Harris |

(Continued)

FOREIGN PATENT DOCUMENTS

| | | |
|---|---|---|
| CN | 101108800 A | 1/2008 |
| EP | 226097 B1 | 5/1990 |

(Continued)

OTHER PUBLICATIONS

Zdena Sedlakova et al., "Synthesis of 2-(2-carboxybenzoyloxy)ethyl methacrylate and its radical polymerization and copolymerization with butyl methacrylate", Wiley Online Library, Mar. 12, 2003, vol. 201, pp. 33-48.
International Search Report mailed Apr. 18, 2014 in PCT application No. PCT/US2013/076131.
"Achieving Optimal Paint Performance: Rheological Modifiers for Water-Reducible OEM Coatings", Oct. 1, 2004.
CAS Registry No. 27697-00-3.
"DECOVERY TM, Urathix® AT231 Q-80, Urathix® AT232 Q-80", DSM NeoResins+, Unlimited. DSM, www.dsmneoresins.com.
"Optigel® / Laponite Rheological Additives for Aqueous Systems",SCP Rockwood Additives.

(Continued)

*Primary Examiner* — Robert Jones, Jr.

(57) ABSTRACT

Disclosed is a pH responsive polymer made with mono-[2-(methacryloyloxy)ethyl]phthalate and/or mono-[2-(methacryloyloxy)ethyl hexahydro]phthalate. Also disclosed is an aqueous coating composition including at least one latex polymer derived from at least one monomer copolymerized or blended with alkali swellable acrylate copolymer. Also provided is an aqueous coating composition including at least one latex polymer derived from at least one monomer blended with alkali swellable acrylate copolymer, at least one pigment, and water. Also provided is a method of preparing an aqueous coating composition such as a latex paint including the above components. Also provided are methods of preparing mono-[2-(methacryloyloxy)ethyl]phthalate. Also provided are compositions and methods using the polymer in hydraulic fracturing, personal care and or home and industrial cleaners.

36 Claims, 4 Drawing Sheets

(56) References Cited

U.S. PATENT DOCUMENTS

| | | | |
|---|---|---|---|
| 5,648,584 | A | 7/1997 | Murray |
| 5,648,585 | A | 7/1997 | Murray |
| 5,674,823 | A | 10/1997 | Ricca et al. |
| 5,770,760 | A | 6/1998 | Robinson |
| 5,849,960 | A | 12/1998 | Singleton et al. |
| 5,874,495 | A | 2/1999 | Robinson |
| 5,942,560 | A * | 8/1999 | Idogawa et al. ............ 523/161 |
| 6,150,222 | A | 11/2000 | Gardner et al. |
| 6,150,312 | A | 11/2000 | Puvvada et al. |
| 6,174,846 | B1 | 1/2001 | Villa |
| 6,222,077 | B1 | 4/2001 | Singleton |
| 7,084,095 | B2 | 8/2006 | Lee et al. |
| 7,217,752 | B2 | 5/2007 | Schmucker-Castner et al. |
| 7,288,616 | B2 | 10/2007 | Tamareselvy et al. |
| 7,378,479 | B2 | 5/2008 | Tamareselvy et al. |
| 7,427,583 | B2 | 9/2008 | Couillet et al. |
| 7,727,937 | B2 | 6/2010 | Pauls et al. |
| 7,772,421 | B2 | 8/2010 | Yang et al. |
| 7,776,318 | B2 | 8/2010 | Bissey-Beugras et al. |
| 7,789,160 | B2 | 9/2010 | Hough et al. |
| 7,857,055 | B2 | 12/2010 | Li |
| 8,071,674 | B2 | 12/2011 | Yang et al. |
| 2003/0068350 | A1 | 4/2003 | Sorrentino et al. |
| 2005/0209382 | A1 | 9/2005 | Yale et al. |
| 2006/0270563 | A1 | 11/2006 | Yang et al. |
| 2007/0014746 | A1 | 1/2007 | Bigorra Llosas et al. |
| 2008/0045646 | A1 | 2/2008 | Tamareselvy |
| 2008/0113895 | A1 | 5/2008 | Tamareselvy et al. |
| 2009/0192051 | A1 | 7/2009 | Carman |
| 2010/0227982 | A1 * | 9/2010 | Inaba et al. ............... 525/410 |
| 2012/0029138 | A1 | 2/2012 | Martinez-Castro et al. |
| 2012/0121523 | A1 | 5/2012 | Yang et al. |
| 2012/0123149 | A1 | 5/2012 | Yang et al. |
| 2014/0178325 | A1 | 6/2014 | Martinez-Castro et al. |

FOREIGN PATENT DOCUMENTS

| | | |
|---|---|---|
| EP | 0444791 A1 | 9/1991 |
| EP | 705852 B1 | 12/1998 |
| EP | 1721915 A1 | 11/2006 |
| EP | 1721915 B1 | 5/2008 |
| EP | 1465932 B1 | 7/2008 |
| EP | 2514777 A1 | 10/2012 |
| JP | S4889947 A | 11/1973 |
| WO | 2008060997 A1 | 5/2008 |
| WO | 2012018384 A2 | 2/2012 |

OTHER PUBLICATIONS

"Honelywell A-C® Performance Additives", Honeywell.
"Carbopole®* Aqua SF-1 Polymer INCI Name: Acrylates Copolymer", The Lubrizol Corporation, noveon Consumer Specialities, Edition: Jul. 2007.
"VISCOGEL SD".
"RHOPLEX™ SG-30 Acrylic Emulsion Meets 150 g / L VOC Regs", DOW.
"IGEPAL® CO-887", Product Data Sheet N000300, CAS No. 68412-54-4, Feb. 2009.
"RHODAPEX AB 20", Product Data Sheet E 90004495, CAS No. 67762-19-0, May 2010.
Apr. 13, 2015, Office Action for U.S. Appl. No. 14/132,893, Nemesio Martinez-Castro et al. filed Dec. 18, 2013.
"Achieving Optimal Paint Performance: Rheological Modifiers for Water-Reducible OEM Coatings", PCI, Painting and Coating Industry Magazine, Oct. 1, 2004, retrieved from the Internet May 5, 2014, URL:< http://www.pcimag.com/articles/84805-achieving-optimal-paint-performance-rheological-modifiers-for-water-reducible-oem-coatings>.
Search Report for CAS Registry No. 27697-00-3, conducted by Applicant (prior to Dec. 21, 2012).
"DECOVERY™, Urathix® AT231 Q-80, Urathix® AT232 Q-80", DSM NeoResins+ Unlimited, DSM (2009), URL:<www.dsmneoresins.com>, retrieved from the Internet May 3, 2012.

* cited by examiner

COMPOSITIONS WITH PH RESPONSIVE COPOLYMER CONTAINING MAEP AND/OR MAHP AND METHOD FOR USING SAME

CROSS-REFERENCE TO RELATED APPLICATION

This claims the benefit of U.S. provisional patent application No. 61/740,837, filed 21 Dec. 2012, incorporated herein by reference.

FIELD OF THE INVENTION

The present invention relates to compositions and methods using a HASE copolymer or ASE copolymer as a thickener for making paints and coatings. In particular one of the monomers from which the HASE and/or ASE copolymer is made is mono-[2-(methacryloyloxy)ethyl]phthalate (MAEP) (also known as 2-(2-carboxybenzoyloxy)ethyl methacrylate) and/or mono-[2-(methacryloyloxy)ethyl hexahydro]phthalate (MAHP) (also known as Monoacryloyloxyethy Hexahydrophthalate).

BACKGROUND OF THE INVENTION

Rheological additives are chemical compositions, which, added even in small amounts, modify a liquid system's rheological properties, such as viscosity and response to shear. Such additives or thickeners may be used in a variety of liquid systems including aqueous systems such as paints, aqueous inks, and personal care products and compositions for treating subterranean formations. The additives improve the rheological properties by also affecting the dispersion, suspension and emulsification of pigments, binders and other solids within a vehicle.

Thixotropic promoters are a category of rheology additives widely used in the coating industry. They can be categorized as organic clay, polyethylene waxes and titanium derivatives. These thixotropic promoters have been used for a long time in latex paints and other architectural coatings. Many types of thixotropic promoters are used because each of them has its own limitations. Some, such as the organic clay, are very effective but they have disadvantages such as decreasing the gloss of the paint significantly. Thixotropic promoters are also used in hydraulic fracturing of subterranean formations, such as oil and natural gas wells, and other methods of secondary oil recovery.

Hydrophobically modified alkali swellable emulsion (HASE, also known as Hydrophobically modified alkali soluble) polymer systems and alkali soluble emulsion (ASE) polymer systems are commonly employed to modify the rheological properties of aqueous emulsion systems. These polymers are substantially insoluble in water at a low pH. However, at higher pH they become swellable or soluble in water and thus exhibit thickening behavior. Under the influence of a base, organic or inorganic, the HASE particles gradually swell and expand to form a three-dimensional network by intermolecular hydrophobic aggregation between HASE copolymer chains and/or with components of the emulsion. This network, combined with the hydrodynamic exclusion volume created by the expanded HASE chains, produces a thickening effect. This network is sensitive to applied stress so it breaks down under shear and recovers when the stress is relieved. Such rheological properties are particularly desirable for paints and coatings because they make the formulation easy to apply onto a surface while providing the thickness needed for uniform coverage and avoid spattering.

These alkali-swellable and alkali-soluble polymers are carboxyl functional polymers synthesized by free radical polymerization. HASE copolymer systems can be prepared from the following monomers: (a) an ethylenically unsaturated carboxylic acid, (b) a nonionic ethylenically unsaturated monomer, and (c) an ethylenically unsaturated hydrophobic monomer. Representative HASE copolymer systems include those shown in EP 226097 B1, EP 705852 B1, U.S. Pat. No. 4,384,096, U.S. Pat. No. 5,874,495, U.S. Pat. No. 7,217,752 B2, and US patent application publication 2006/0270563 A1, now U.S. Pat. Nos. 7,772,421 and 8,071,674, all incorporated herein by reference.

Three categories of polymers produced by emulsion polymerization are: (1) Synthetic rubber: some grades of styrene-butadiene (SBR), some grades of polybutadiene, polychloroprene (Neoprene), nitrile rubber, acrylic rubber, fluoroelastomer (FKM); (2) Plastic: some grades of PVC, some grades of polystyrene, some grades of PMMA (polymethylmethacrylate), acrylonitrile-butadiene-styrene terpolymer (ABS), polyvinylidene fluoride, polytertrafluoroethylene (PTFE); and (3) Dispersions (i.e., polymers sold as aqueous dispersions).

Latex is an example of an emulsion polymer which is a water based polymer dispersion. Latex paints are used for a variety of applications including interior and exterior, and flat, semi-gloss and gloss applications. Latex is a stable dispersion (colloidal emulsion) of rubber or plastic polymer microparticles in an aqueous medium. Latexes may be natural or synthetic.

It would be desirable to have a as a thixotropic promoter that provides improved viscosity control, sagging, and leveling, while maintaining gloss in latex paints and coatings.

Hydraulic fracturing of the subterranean formation is conducted to increase oil and/or gas production. Fracturing is caused by injecting a viscous fracturing fluid or a foam at a high pressure (hereinafter injection pressure) into the well to form a fracture. As the fracture is formed, the particulate material, referred to as a "propping agent" or "proppant" is placed in the formation to maintain the fracture in a propped condition when the injection pressure is released. Coated and/or uncoated particles are often used as proppants to keep open fractures imposed by hydraulic fracturing upon a subterranean formation, e.g., an oil or gas bearing strata. Particles typically used to prop fractures generally comprise sand or sintered ceramic particles as the fracture forms, the proppants are carried into the fracture by suspending them in additional fluid or foam to fill the fracture with slurry of proppant in the fluid or foam. Upon release of the pressure, the proppants form a pack that serves to hold open the fractures. Thus, the proppants increase production of oil and/or gas by providing a conductive channel in the formation. There is a need for a proppant carrier that can prevent settling of proppants or sand being positioned in the fractures.

During primary recovery a subterranean formation produces the oil by pressure depletion. In pressure depletion, the pressure difference between the formation and a production well or wells forces the oil contained within the formation toward a production well where it can be recovered. Typically, up to 35 percent of the oil initially contained in a formation can be recovered using pressure depletion. Methods have been developed to recover oil which could not be recovered using only pressure depletion techniques or secondary recovery techniques. These methods are typically referred to as "enhanced oil recovery techniques" (EOR).

One enhanced oil recovery process is referred to as surfactant flooding. This generally covers the use of an aqueous fluid containing surfactant injected into an oil rich formation to displace oil from the formation and the displaced oil is then recovered.

Another enhanced oil recovery process is referred to as chemical flooding. This generally covers the use of polymer and/or surfactant slugs. In polymer flooding, a polymer solution is injected to displace oil toward producing wells. The polymer solution is designed to develop a favorable mobility ratio between the injected polymer solution and the oil/water bank being displaced ahead of the polymer. In surfactant flooding, an aqueous solution containing surfactant is injected into the oil rich formation. Residual oil drops are deformed as a result of low interfacial tension provided by surfactant solution and drops are displaced through the pore throats and displaced oil is then recovered.

U.S. Pat. No. 4,432,881, incorporated herein by reference in its entirety, discloses an aqueous liquid medium having increased low shear viscosity as provided by dispersing into the aqueous medium (1) a water-soluble polymer having pendant hydrophobic groups, e.g., an acrylamide dodecyl acrylate copolymer, and (2) a water-dispersible surfactant, e.g., sodium oleate, or dodecyl polyethyleneoxy glycol monoether.

U.S. Pat. No. 4,541,935, incorporated herein by reference in its entirety, discloses fracturing processes which use aqueous hydraulic fracturing fluids. The fluids comprise: (a) an aqueous medium, and (b) a thickening amount of a thickener composition comprising (i) a water-soluble or water-dispersible interpolymer having pendant hydrophobic groups chemically bonded thereto, (ii) a nonionic surfactant having a hydrophobic group(s) capable of associating with the hydrophobic groups on said organic polymer, and (iii) a water-soluble electrolyte.

U.S. Pat. No. 5,566,760, incorporated herein by reference in its entirety, discloses a fracturing fluid comprising surfactants and hydrophobically-modified polymers.

U.S. Pat. No. 7,084,095, incorporated herein by reference in its entirety, discloses addition of polymers to a viscoelastic surfactant base system allows adjusting the rheological properties of the base fluid.

U.S. Pat. No. 7,427,583, incorporated herein by reference in its entirety, describes an aqueous viscoelastic fracturing fluid for use in the recovery of hydrocarbons. The fluid comprises a viscoelastic surfactant and a hydrophobically modified polymer.

U.S. Pat. No. 7,727,937 to Pauls et al, incorporated herein by reference in its entirety, discloses acidic treatment fluids used in industrial and/or subterranean operations, and more particularly, acidic treatment fluids comprising clarified xanthan gelling agents, and methods of use in industrial and/or subterranean operations.

U.S. Pat. No. 7,772,421 to Yang et al, incorporated herein by reference in its entirety, discloses a hydraulic fracturing composition comprising water, a pH responsive polymer and a proppant.

U.S. Pat. No. 7,789,160 to Hough et al, incorporated herein by reference in its entirety discloses an aqueous fluid useful for the recovery of crude oil from a subterranean formation, which includes a composition including a mixture of water, a water soluble block copolymer, an inorganic salt and at least one member of the group of a nonionic surfactant having an HLB of less than 12, and methods for using same.

U.S. Pat. No. 7,857,055 to Li et al, incorporated herein by reference in its entirety, discloses a fluid for treating a subterranean formation comprising an aqueous solution of a polysaccharide, a polyacrylamide, a crosslinking agent, and less than 0.1% by weight of any clay component, wherein the polyacrylamide is present in an amount of from about 0.01 percent to about 1 percent by weight of the fluid.

It would be desirable to provide stable fracturing fluids and EOR fluids for subterranean formations, such as natural gas and/or oil field.

Also, there is a need to enhance viscosity to improve personal care compositions. In personal care applications, consumers are increasingly demanding formulations that provide multiple benefits such as, but not limited to, unique sensory experience, enhanced moisturization, increased conditioning, improved delivery of active ingredients and compatibility. Synthetic rheology modifier polymers can be employed to assist in achieving one or more of these properties.

Also there is a need to enhance viscosity to improve cleaning compositions for home and industry.

SUMMARY OF THE INVENTION

The invention is directed to pH responsive copolymer of a mixture of unsaturated copolymerizable monomers, the unsaturated copolymerizable monomers comprising, based on total weight of monomers:

A. about 0.1-70 weight percent, typically 0.5-50, 0.7-40, 1-40, 5-40, 5-30 or 10 to 40 weight percent of at least one alpha beta-ethylenically unsaturated first acid monomer selected from the group consisting of mono-[2-(methacryloyloxy)ethyl]phthalate (also known as 2-(2-carboxybenzoyloxy)ethyl methacrylate, MAEP) and mono-[2-(Methacryloyloxy)ethyl hexahydro]phthalate (MAHP), B. about 0-45 weight percent, preferably 5 to 30 weight percent, of at least one C3-C8 alpha beta-ethylenically unsaturated acidic monomer, preferably a C3-C8 alpha beta-ethylenically unsaturated carboxylic acid monomer;

C. about 15-70 weight percent, typically 20 to 50 weight percent, of at least one non-ionic, copolymerizable C2-C12 alpha, beta-ethylenically unsaturated monomer; and D. about 0 to 30 weight percent, preferably 0.05 to 30 weight percent or typically 5 to 20 weight percent, of at least one non-ionic ethylenically unsaturated hydrophobic monomer.

The pH responsive copolymer is also known as a HASE or ASE copolymer. The HASE copolymer includes component D and the ASE copolymer does not include component D.

The present invention also includes compositions such as aqueous dispersions comprising this pH responsive copolymer. In particular the invention is also directed using the pH responsive copolymer as an additive for latex binders, paints and aqueous coatings. This pH responsive copolymer additive is a thickener used as a thixotropic promoter during formulation of the latex binders, paints and aqueous coatings, compositions for treating subterranean formations, home care and personal care.

The invention is also directed to a homogeneous, pourable liquid which improves sagging properties in coatings without a significant decrease in gloss. The improved sagging property is due to the thixotropic behavior of the HASE and/or ASE copolymer thickener synthesized with the above mentioned monomer. In addition the new thixotropic promoter only needs low shear for incorporation.

The aqueous coating compositions of the invention typically include at least one latex polymer derived from at least one monomer, for example acrylic monomers. The at least one latex polymer in the aqueous coating composition can be a pure acrylic, a styrene acrylic, a vinyl acrylic or an acrylated ethylene vinyl acetate copolymer and is more preferably a pure acrylic. The at least one latex polymer is preferably derived from at least one acrylic monomer selected from the group consisting of acrylic acid, acrylic acid esters, methacrylic acid, and methacrylic acid esters. For example, the at least one latex polymer can be a butyl acrylate/methyl methacrylate copolymer or a 2-ethylhexyl acrylate/methyl methacrylate copolymer. Typically, the at least one latex polymer is further derived from one or more monomers selected from the group consisting of styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, and C4-C8 conjugated dienes.

Latex paint formulations typically comprise additives, e.g., at least one pigment. In a preferred embodiment of the invention the latex paint formulation includes at least one pigment selected from the group consisting of TiO2, CaCO3, clay, aluminum oxide, silicon dioxide, magnesium oxide, sodium oxide, potassium oxide, talc, barytes, zinc oxide, zinc sulfite and mixtures thereof. More preferably the at least one pigment includes TiO2, calcium carbonate or clay.

In addition to the above components, the aqueous coating composition can include one or more additives selected from the group consisting of dispersants, surfactants, rheology modifiers, defoamers, thickeners, biocides, mildewcides, colorants, waxes, perfumes and co-solvents.

The present invention is also directed to new processes for making mono-[2-(methacryloyloxy)ethyl]phthalate (also known as 2-(2-carboxybenzoyloxy)ethyl methacrylate, MAEP).

Compositions of the present invention may have an absence of one or more of anionic surfactant, cationic surfactant, nonionic surfactant, zwitterionic surfactant, and/or amphoteric surfactant.

These and other features and advantages of the present invention will become more readily apparent to those skilled in the art upon consideration of the following detailed description, which describe both the preferred and alternative embodiments of the present invention.

DETAILED DESCRIPTION OF THE PREFERRED EMBODIMENTS

Figure 1:
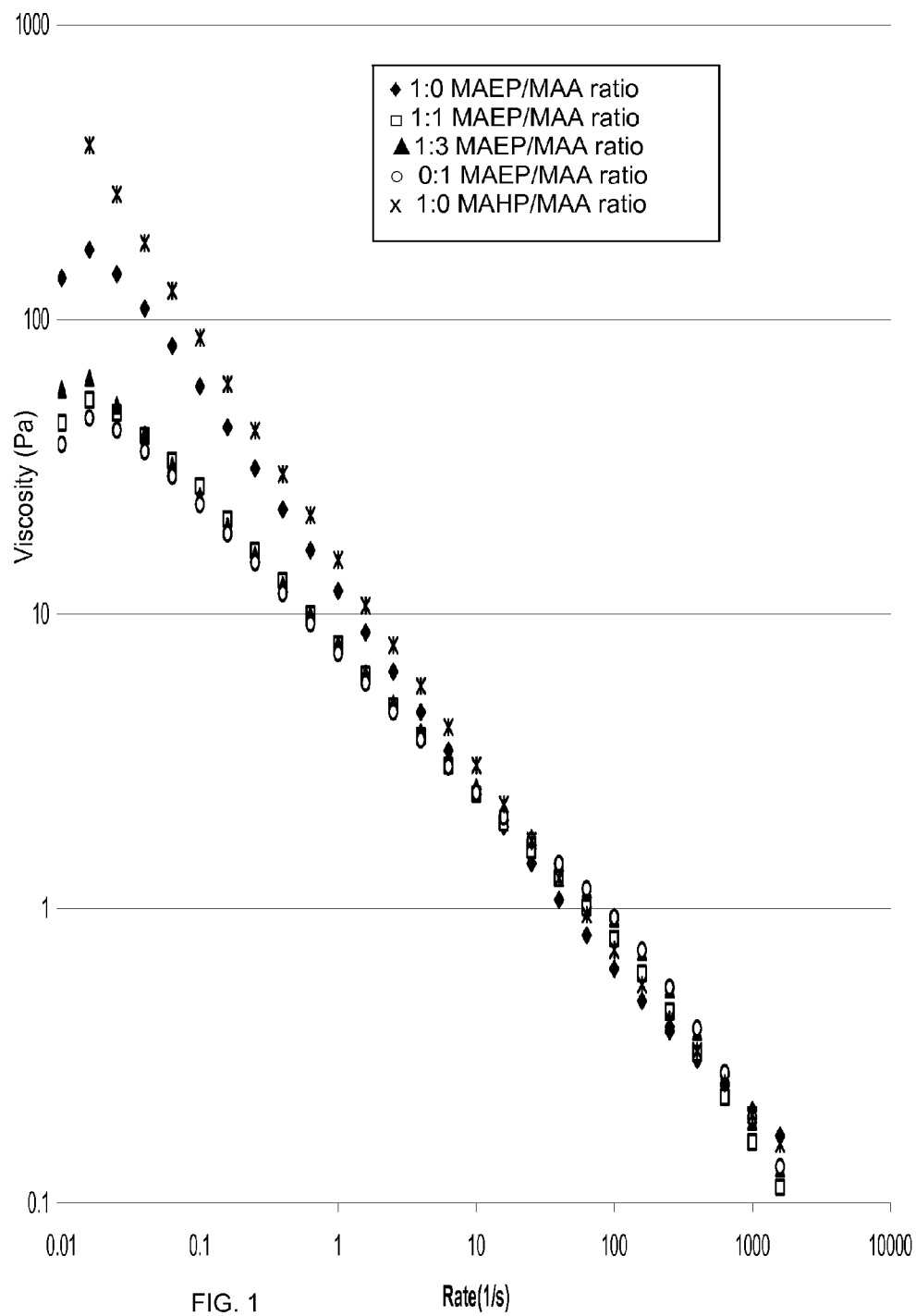
FIG. 1 shows Viscosity Profiles of formulations prepared with HASE thickeners containing MAEP and MAHP (in RHOPLEX SG30).

The present invention relates to the use of a particular family of HASE and/or ASE copolymers for latex dispersions, binders, paints and coatings. The present invention provides aqueous compositions, for example, aqueous coating compositions. The aqueous compositions of the invention are aqueous polymer dispersions which include at least one latex polymer. Paints or other aqueous coatings of the present invention typically further include at least one pigment. Typically the latex has a Tg of less than 10° C., more typically less than 5° C., still more typically in the range from 5 to −10° C., e.g., 0° C.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tetracontyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "arylalkyl" means an alkyl group substituted with one or more aryl groups, more typically a ($C_1$-$C_{18}$)alkyl substituted with one or more ($C_6$-$C_{14}$)aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

The "bicyclo[d.e.f]" notation is used herein in reference to bicycloheptyl and bicycloheptenyl ring systems in accordance with the von Baeyer system for naming polycyclic compounds, wherein a bicyclic system is named by the prefix "bicyclo-" to indicate number of rings in the system, followed by a series of three arabic numbers, listed in descending numerical order, separated by full stops, and enclosed in square brackets, to indicate the respective number of skeletal atoms in each acyclic chain connecting the two common atoms (the "bridgehead atoms"), excluding the bridgehead atoms.

A bridgehead atom is any skeletal atom of the ring system bonded to three or more skeletal atoms (excluding hydrogen). A bicyclic system (which comprises the main ring and main bridge only) is named by: the prefix bicyclo-(indicating the number of rings); numbers indicating the bridge lengths (i.e. number of skeletal atoms excluding the bridgehead atoms) separated by full stops and placed in square brackets. The three numbers are cited in decreasing order of size (e.g. [3.2.1]); the name of the hydrocarbon indicating the total number of skeletal atoms. For example, bicyclo[3.2.1]octane is the name for the structure of Formula I.

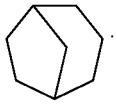

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$)alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a ($C_1$-$C_{22}$)alkyl radical, that is substituted with one or more hydroxyl groups, such as for example, hydroxymethyl, hydroxyethyl, hydroxypropyl, and hydroxydecyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl(meth)acrylate" means butyl acrylate and/or butyl methacrylate.

As used herein, "molecular weight" in reference to a polymer or any portion thereof, means to the weight-average molecular weight ("$M_w$") of the polymer or portion. $M_w$ of a polymer is a value measured by gel permeation chromatography (GPC) with an aqueous eluent or an organic eluent (for example dimethylacetamide, dimethylformamide, and the like), depending on the composition of the polymer, light scattering (DLS or alternatively MALLS), viscometry, or a number of other standard techniques. $M_w$ of a portion of a polymer is a value calculated according to known techniques from the amounts of monomers, polymers, initiators and/or transfer agents used to make the portion.

In one embodiment, the copolymers for use in the present invention exhibit a weight average molecular weight, as determined by gel permeation chromatography (GPC) and light scattering of a solution of the polymer in tetrahydrofuran and compared to a polystyrene standard, of greater than or equal to 30,000 grams per mole ("g/mole"). HASE thickeners may not fully dissolve in THF but after hydrolysis they can dissolve in water and measurement can be run in a water gel permeation chromatography (GPC). Reference: Macromolecules 2000, 33, 2480. For example in a range of 30,000 to 2,000,000 g/mole.

As used herein, the indication that a radical may be "optionally substituted" or "optionally further substituted" means, in general, unless further limited either explicitly or by the context of such reference, such radical may be substituted with one or more inorganic or organic substituent groups, for example, alkyl, alkenyl, aryl, arylalkyl, alkaryl, a hetero atom, or heterocyclyl, or with one or more functional groups capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

As used herein, the term "surfactant" means a compound that reduces surface tension when dissolved in water.

"Surfactant effective amount" means the amount of the surfactant that provides a surfactant effect to enhance the stability of emulsions of the polymers.

I. pH Responsive Copolymer

The invention is directed to a pH responsive copolymer of a mixture of unsaturated copolymerizable monomers. These pH responsive copolymers are substantially insoluble in water at a low pH. However, at higher pH they become swellable or soluble in water and thus exhibit thickening behavior. Thus, the pH responsive copolymer is interchangeably termed alkali swellable copolymer or alkali soluble copolymer. Typically the pH responsive copolymer is termed an alkali-soluble emulsion (ASE) copolymer and/or a hydrophobically modified alkali-soluble emulsion (HASE) copolymer. Although this copolymer is described as ASE and/or HASE copolymer it is not necessary to make a copolymer of this structure by emulsion polymerization. The copolymer may also be made by solution polymerization and comes within the invention whether made by emulsion polymerization or solution polymerization.

The pH responsive copolymer is made from a mixture of unsaturated copolymerizable monomers, the unsaturated copolymerizable monomers comprising, based on total weight of monomers:

A. about 0.1-70 weight percent, typically 0.5-50, 0.7-40, 1-40, 5-40, 5-30 or 10 to 40 weight percent, of at least one alpha beta-ethylenically unsaturated first acid monomer selected from the group consisting of mono-[2-(methacryloyloxy)ethyl]phthalate (MAEP) (also known as 2-(2-carboxybenzoyloxy)ethyl methacrylate, MAEP) having the structure A.I:

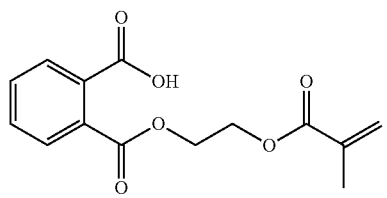

A.I

CAS No. 27697-00-3; Chemical Formula C14H14O6; molecular weight 278.08; and mono-[2-(methacryloyloxy)ethyl hexahydro]phthalate (MAHP) (also known as Monoacryloyloxyethy Hexahydrophthalate) having the structure A.II

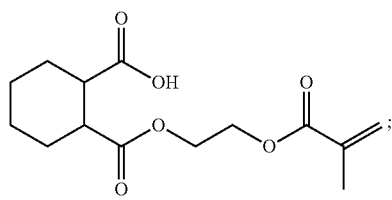

A.II

CAS No. 51252-88-1, molecular formula C14H20O6, molecular weight 284.31.

B. about 0-45 weight percent, preferably 5 to 30 weight percent, of at least one C3-C8 alpha, beta-ethylenically unsaturated first acidic monomer, preferably a C3-C8 alpha beta-ethylenically unsaturated carboxylic acid monomer;

C. about 15-70 weight percent, typically 20 to 50 weight percent, of at least one nonionic monomer, each comprising a nonionic substituent group, copolymerizable C2-C12 alpha, beta-ethylenically unsaturated monomer; and D. about 0 to 30 weight percent, preferably 0.05 to 30 weight percent or typically 5 to 20 weight percent, of at least one non-ionic ethylenically unsaturated hydrophobic monomer.

In terms of monomeric units of the resulting pH responsive copolymer, rather than monomers from which the pH responsive copolymer is made, the pH responsive copolymer comprises:

A. about 0.1-70 weight percent, typically 0.5-50, 0.7-40, 1-40, 5-40, 5-30 or 10 to 40 weight percent first acidic monomeric units derived by opening the alpha beta-ethylenic unsaturated bond of at least one member of the group consisting of mono-[2-(methacryloyloxy)ethyl]phthalate (also known as 2-(2-carboxybenzoyloxy)ethyl methacrylate, MAEP) mono-[2-(Methacryloyloxy)ethyl hexahydro]phthalate (MAHP);

B. about 0-45 weight percent, preferably 5 to 30 weight percent, second acidic monomeric units, preferably each second acidic monomeric unit independently comprises a carboxylic acid-functional substituent group;

C. about 15-70 weight percent, typically 20 to 50 weight percent, nonionic monomeric units, each comprising a nonionic substituent group. The non-ionic monomeric units, each independently comprising a nonionic substituent group, for example Ethyl Acrylate (EA) monomer; and D. about 0 to 30 weight percent, preferably 0.05 to 30 weight percent or typically 5 to 20 weight percent, of at least one non-ionic ethylenically unsaturated hydrophobic monomeric unit.

The ASE copolymer lacks the non-ionic ethylenically unsaturated hydrophobic monomeric units. In contrast, the HASE copolymer includes the hydrophobic monomeric units in an amount of about 0.05-30 weight percent hydrophobic monomer units based on total weight of monomers.

The first acidic monomeric units assist to prevent sagging.

The second acidic monomeric units provide solubility and sagging. Typical second acidic monomeric units each independently comprise at least one acid group per monomeric unit, for example, a sulfonic acid group, a phosphonic acid group, a phosphoric acid group, or a carboxylic acid-functional substituent group. Typically the second acidic monomeric units, each independently comprise a carboxylic acid-functional substituent group, for example, methacrylic acid (MAA).

The nonionic monomeric units, for example slightly insoluble ethyl acrylate (EA) or butyl acrylate (BA), segments enhance the thickening performance by promoting hydrophobic aggregations.

The hydrophobic macro monomers are responsible for intra-/intermolecular associations. For example, they are specialty monomers which typically include a polymerizable group, a hydrophobic macro group and a bivalent polyether group of a poly(ethylene oxide) chain, usually 5-100 ethylene oxide units (typically 6-10 EO groups) and optionally 0-5 propylene oxide units to favor the intermolecular aggregation. The bivalent polyether group typically links the hydrophobic macro groups to the polymerizable group. The polymerizable group typically becomes part of the backbone of the pH responsive copolymer and the bivalent polyether group linking group and macro group becomes a side chain of the pH responsive copolymer. Examples of this side chain comprising the bivalent polyether group linking group and macro group are a bicycloheptyl-polyether group, a bicycloheptenyl-polyether group or a branched ($C_5$-$C_{50}$)alkyl-polyether group, wherein the bicycloheptyl-polyether or bicycloheptenyl-polyether group may optionally be substituted on one or more ring carbon atoms by one or two ($C_1$-$C_6$)alkyl groups per carbon atom.

Formula III shows an idealized diagram of the structure of an embodiment of this HASE copolymer made from alpha beta-ethylenic unsaturated bond of mono-[2-(methacryloyloxy)ethyl]phthalate (also known as 2-(2-carboxybenzoyloxy)ethyl methacrylate, MAEP) as the first acidic monomer, methacrylic acid as the second acidic monomer, ethyl acrylate as the nonionic monomer and a hydrophobic polymer. The hydrophobic polymer having a polyethylene oxide chain as a bivalent polyether group linking a polymerizable functional group and a C18H37 macro hydrophobic group.

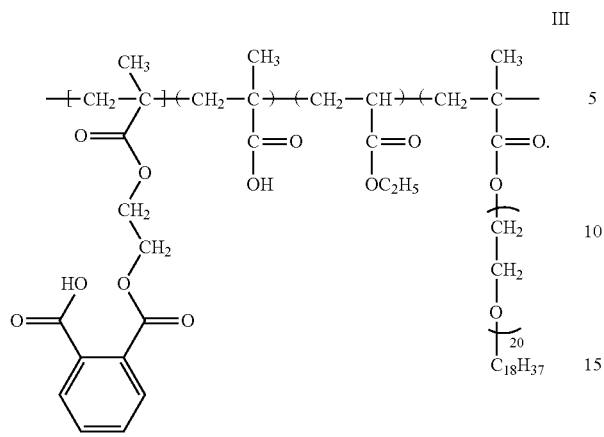

III

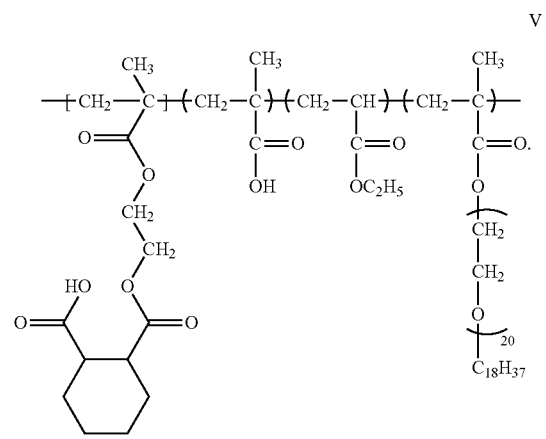

V

Formula IV shows an idealized diagram of the structure of an ASE copolymer made from alpha beta-ethylenic unsaturated bond of mono-[2-(methacryloyloxy)ethyl]phthalate (also known as 2-(2-carboxybenzoyloxy)ethyl methacrylate, MAEP) as the first acidic monomer, methacrylic acid as the second acidic monomer, ethyl acrylate as the nonionic monomer, and a hydrophobic polymer having a polymerizable functional group, a C18H37 macro hydrophobic group and an ethylene oxide chain as a bivalent polyether group linking the polymerizable functional group and a C18H37 macro hydrophobic group.

Formula VI shows an idealized diagram of the structure of an ASE copolymer made from mono-[2-(Methacryloyloxy) ethyl hexahydro]phthalate (MAHP) as the first acidic monomer, methacrylic acid as the second acidic monomer, ethyl acrylate as the nonionic monomer, and a hydrophobic polymer having a polymerizable functional group, a C18H37 macro hydrophobic group and an ethylene oxide chain as a bivalent polyether group linking the polymerizable functional group and a C18H37 macro hydrophobic group.

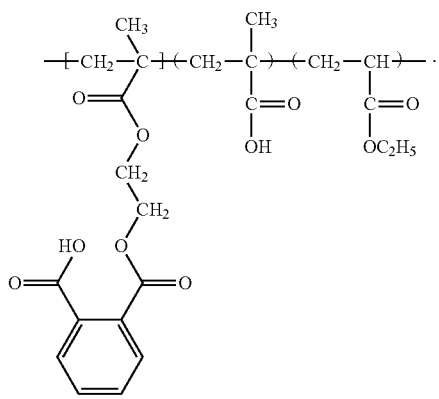

IV

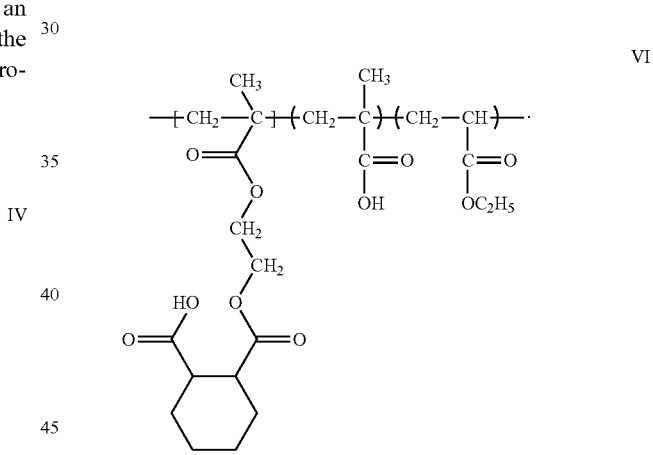

VI

Formula V shows an idealized diagram of the structure of this HASE copolymer made from alpha beta-ethylenic unsaturated bond of mono-[2-(Methacryloyloxy)ethyl hexahydro] phthalate (MAHP) as the first acidic monomer, methacrylic acid as the second acidic monomer, ethyl acrylate as the nonionic monomer, and a hydrophobic polymer having a polymerizable functional group, a C18H37 macro hydrophobic group and an ethylene oxide chain as a bivalent polyether group linking the polymerizable functional group and a C18H37 macro hydrophobic group.

The ASE and/or HASE copolymer comprises a chain of monomeric units. The polymer is a macromolecule having a relatively high molecular mass that comprises chains of multiple repetitions of the monomeric units, which are derived, actually or conceptually, from molecules of relatively low molecular mass and are connected to form a linear, branched, or network structure. The copolymer typically has a linear or branched structure, more typically single strand linear or branched structure. In one embodiment, a polymer having a predominantly single strand linear or branched structure is lightly crosslinked to form a polymer network having a low density of crosslinks. As used herein the term "single strand" in regard to a polymer means monomeric units of the polymer are connected such that adjacent monomeric units are joined to each other through two atoms, one on each of the adjacent monomeric units.

The copolymer may typically be regarded as having a "backbone", or main polymer chain, from which all branches and substituent groups of the polymer may be regarded as being pendant. Where two or more chains of the copolymer could equally be considered to be the main chain of the polymer, that chain is selected as the main chain which leads to the simplest representation of the polymer molecule. The monomeric units of the copolymer may be arranged in random, alternating, tapered, or block sequence along the copolymer chain.

The ASE and/or HASE copolymer typically has a weight average molecular weight of greater than or equal to about 30,000 grams per mole, typically the copolymer has a weight average molecular weight of greater than or equal to about 30,000 to 1,000,000 grams per mole or 30,000 to 500,000 grams per mole or 50,000 to 500,000 grams per mole.

A. First Acidic Monomers for pH Responsive Copolymer

The alpha beta-ethylenically unsaturated first acid monomer is selected from the group consisting of mono-[2-(methacryloyloxy)ethyl]phthalate (also known as 2-(2-carboxybenzoyloxy)ethyl methacrylate, MAEP) and mono-[2-(Methacryloyloxy)ethyl hexahydro]phthalate (MAHP).

Mono-[2-(Methacryloyloxy)ethyl hexahydro]phthalate (MAHP) has the structure A.II:

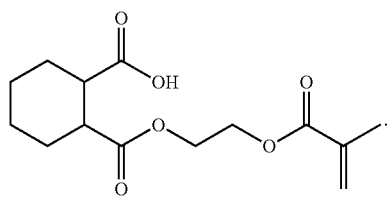

A.II

It is commercially available from Wako Pure Chemical Industries.

It has the CAS No. 51252-88-1, the molecular formula C14H20O6, and a molecular weight of 284.31 g/mol.

Mono-[2-(methacryloyloxy)ethyl]phthalate has the structure A.I:

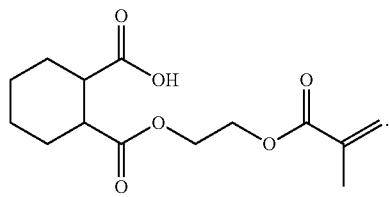

A.I

MAEP has the chemical formula C14H14O6 and a molecular weight of 278.08 g/mol.

There are a number of routes to making mono-[2-(methacryloyloxy)ethyl]phthalate. For example it can be made by method AA:

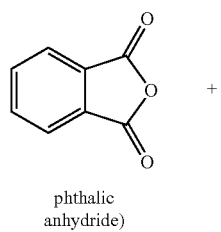

AA phthalic anhydride)

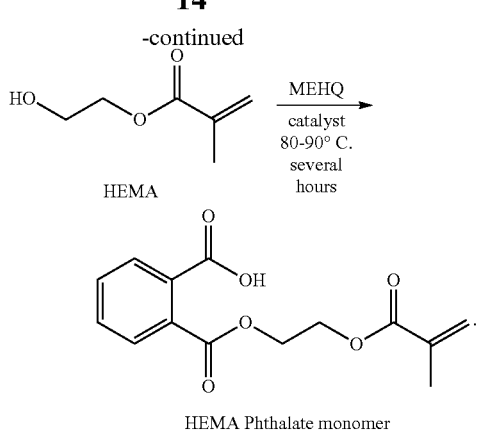

MEHQ is mono methyl ether of hydroquinone (also known as 4-methoxy phenol). It is an inhibitor to prevent Hydroxyethylmethacrylate (HEMA) and HEMA Phthalate monomer from self reacting.

There are various methods to make mono-[2-(methacryloyloxy)ethyl]phthalate while using a catalyst to lower reaction temperatures. For example, U.S. Pat. No. 3,689,427 (Aug. 27, 1969) discloses synthesis using catalytic N,N-dimethylbenzylamine and no solvent. JP48089947 (1973) discloses synthesis using catalytic triethylamine and no solvent. CN10110880 (Jun. 21, 2007) discloses synthesis using organic solvent and several catalysts including pyridine, ethylenediamine and triethylenediamine. Sedlakova et al., Synthesis of 2-(2-carboxybenzoyloxy)ethyl methacrylate and its radical polymerizatin and copolymerization with butyl methacrylate, *Die Angewandte Makromolekulare Chemie,* 201, 33-48 (1992) discloses synthesis using organic solvent, and several catalysts including pyridine, triethylamine and p-toluenesulfonic acid. All of these patents, patent applications and non-patent literature are incorporated herein by reference.

1. Processes Using Imidazole

A novel process of the present invention for making mono-[2-(methacryloyloxy)ethyl]phthalate employs imidazole to serve as a nucleophile catalyst to activate phthalic anhydride and then as a leaving group on acylated intermediate. This process employing imidazole also employs MEHQ as an inhibitor to prevent HEMA from self reacting.

The use of imidazole in activation of anhydrides within analytical procedures is documented by Evtushenko et al, *Chemistry of Heterocyclic Compounds* 2000, 36, 1054 and Carey et al, *Journal of Cellular Plastics* 1984, January-February. This reference describes imidazole as a useful catalyst in activating anhydrides. However, this reference does not reveal the use of imidazole to synthesize mono-[2-(methacryloyloxy)ethyl]phthalate.

This process comprises the steps of:

mixing 100 parts by weight 2-hydroxyethy methacrylate (HEMA) and 0.1 to 0.5 parts by weight 4-methoxyphenol (MEHQ) to form a mixture;

heating the mixture to a set point of 70-100° C. and then adding 25-50 parts by weight phthalic anhydride as a first dose of phthalic anhydride to the heated mixture;

after adding the first dose of phthalic anhydride then adding 1-3 parts by weight imidazole to the mixture during which an exotherm was noted;

after adding the imidazole then adding 50 to 90 parts by weight phthalic anhydride as a second dose of phthalic anhydride;

after adding the second dose of phthalic anhydride then heating the reaction mixture at 70-90° C. for several hours to form mono-[2-(methacryloyloxy)ethyl]phthalate; and recovering the mono-[2-(methacryloyloxy)ethyl]phthalate.

The reaction mixture was sparged with 8% oxygen in nitrogen throughout the process However, the reaction also works without NOx (92/2 $N_2/O_2$).

2. Process using 2,6-di-tert-butyl-4-(dimethylaminomethyl)phenol or 2,4,6-tris(dimethylaminomethyl)phenol with an absence of MEHQ and an absence of base catalyst Another preferred novel process of the present invention for making mono-[2-(methacryloyloxy)ethyl]phthalate uses 2,6-di-tert-butyl-4-(dimethylaminomethyl)phenol or 2,4,6-tris(dimethylaminomethyl)phenol without MEHQ or base catalyst. In this role they serve as both catalyst and inhibitor.

This process comprises using 2,6-di-tert-butyl-4-(dimethylaminomethyl)phenol or 2,4,6-tris(dimethylaminomethyl)phenol as a catalyst to activate phthalic anhydride and as an inhibitor to prevent HEMA from self-reacting in the absence of additional catalyst. Thus, in this process there is an absence of MEHQ and an absence of base catalyst. The 2,6-di-tert-butyl-4-(dimethylaminomethyl)phenol or 2,4,6-tris(dimethylaminomethyl)phenol each have dual functionality in this process. In particular they each act as a catalyst for the desired reaction of phthalic anhydride and HEMA and an inhibitor to prevent HEMA from self reacting. As sterically hindered phenols, both have the recognized ability to serve as radical inhibitors, inhibiting HEMA from self-reacting.

2,6-di-tert-butyl-4-(dimethylaminomethyl)phenol has formula A.III:

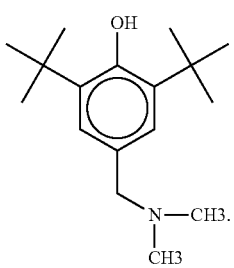

A.III 2,4,6-tris(dimethylaminomethyl)phenol has the following formula A.IV:

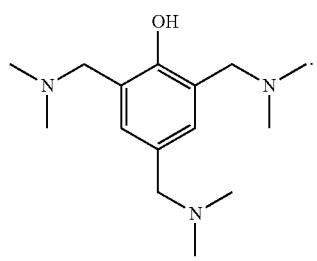

A.IV

This process comprises the steps of:
mixing 15-25 parts by weight 2-hydroxyethy methacrylate (HEMA) and at least one member of the group consisting of 1-3 parts by weight 2,6-di-tert-butyl-4-((dimethylamino)methyl)phenol or 0.2-2 parts by weight 2,4,6-tris((dimethylamino)methyl)phenol;

heating the mixture to a set point of 70-100° C. and then adding 10-30 parts by weight phthalic anhydride to the heated mixture;

after adding the phthalic anhydride then heating the reaction mixture at 70-90° C. for several hours to form mono-[2-(methacryloyloxy)ethyl]phthalate; and recovering the mono-[2-(methacryloyloxy)ethyl]phthalate.

The reaction mixture was sparged with 8% oxygen in nitrogen (NOx) throughout the process.

3. Process using 2,6-di-tert-butyl-4-(dimethylaminomethyl)phenol or 2,4,6-tris(dimethylaminomethyl)phenol with MEHQ in the absence of base catalyst In another inventive process of the present invention, both 2,6-di-tert-butyl-4-(dimethylaminomethyl)phenol or 2,4,6-tris(dimethylaminomethyl)phenol could be used in the presence of MEHQ and in an absence of organic base catalyst to make MAEP. In this role they serve as catalyst only.

This process for making mono-[2-(methacryloyloxy)ethyl]phthalate comprises using 2,6-di-tert-butyl-4-(dimethylaminomethyl)phenol or 2,4,6-tris(dimethylaminomethyl)phenol as a catalyst to activate phthalic anhydride with MEHQ but without organic base (catalyst) on commercially available reagents. In this process MEHQ is employed as a polymerization inhibitor to prevent HEMA from self reacting.

The process comprises the steps of:
mixing 15-25 parts by weight 2-hydroxyethy methacrylate (HEMA) and at least one member of the group consisting of 1-3 parts by weight 2,6-di-tert-butyl-4-((dimethylamino)methyl)phenol or 0.2-2 parts by weight 2,4,6-tris((dimethylamino)methyl)phenol;

heating the mixture to a set point of 70-100° C. with NOx sparge and then adding 10-30 parts by weight phthalic anhydride to the heated mixture;

after adding the phthalic anhydride then heating the reaction mixture at 70-90° C. to form mono-[2-(methacryloyloxy)ethyl]phthalate; and recovering the mono-[2-(methacryloyloxy)ethyl]phthalate, wherein the process steps are performed in the absence of a base catalyst.

Thus, a) these two molecules 2,6-di-tert-butyl-4-(dimethylaminomethyl)phenol or 2,4,6-tris(dimethylaminomethyl)phenol have the following two functions:

1. polymerization inhibitor (due to phenyl ring and OH)
2. monomer reaction catalyst (due to amino groups) to make MAEP b) Either 2,6-di-tert-butyl-4-(dimethylaminomethyl)phenol or 2,4,6-tris(dimethylaminomethyl)phenol can be used to synthesize the monomer MAEP and no additional base catalyst is needed.

c) However, as explained below, monomer could be also synthesized by using the 2,6-di-tert-butyl-4-(dimethylaminomethyl)phenol or 2,4,6-tris(dimethylaminomethyl)phenol molecules and an additional base catalyst.

4. Process using 2,6-di-tert-butyl-4-(dimethylaminomethyl)phenol or 2,4,6-tris(dimethylaminomethyl)phenol with base catalyst In another alternative both 2,6-di-tert-butyl-4-(dimethylaminomethyl)phenol or 2,4,6-tris(dimethylaminomethyl)

phenol could be used in the presence of base catalyst to make MAEP. In this role they serve as an inhibitor. Being an inhibitor is a known literature established role for these reagents.

The base catalyst promotes the formation of product at a lower temperature or in shorter time frame than in an uncatalyzed system. When added to our system, lower reaction temp provided higher quality product than uncatalyzed system. The base catalyst is a Lewis base catalyst. A Lewis base is any species that donates a pair of electrons to a Lewis acid to form a Lewis adduct. For example, OH⁻ and NH₃ are Lewis bases, because they can donate a lone pair of electrons. Lewis base catalysis is the process by which an electron pair donor increases the rate of a given chemical reaction by interacting with an acceptor atom in one of the reagents or substrates. The binding event may enhance either the electrophilic or nucleophilic character of the bound species. Furthermore, the Lewis base should not be consumed or altered during the course of the reaction. A Lewis base is an atomic or molecular species where the highest occupied molecular orbital is highly localized. Typical Lewis bases are amines such as ammonia and alkyl amines. Other common Lewis bases include pyridine and its derivatives. Some of the main classes of Lewis bases are amines of the formula $NH_{3-x}R_x$, where R=alkyl or aryl, for example C10-C2 alkyl or C10-C2 aryl. Related to these are pyridine and its derivatives; phosphines of the formula $PR_{3-x}A_x$, where R=alkyl, A=aryl; and compounds of O, S, Se and Te in oxidation state 2, including water, ethers, ketones. The following amines are typical base catalysts: triethylamine and imidazole.

This process for making mono-[2-(methacryloyloxy) ethyl]phthalate comprises using 2,6-di-tert-butyl-4-(dimethylaminomethyl)phenol or 2,4,6-tris(dimethylaminomethyl)phenol as a catalyst to activate phthalic anhydride with MEHQ (polymerization inhibitor) and organic base (catalyst) on commercially available reagents. In this process MEHQ is employed as an inhibitor to prevent HEMA from self-reacting.

B. Second Acidic Monomeric Units for ASE or HASE Copolymer

The polymer of the present invention optionally further comprises second acidic monomeric units, each independently comprising at least one acid group per second acidic monomeric unit.

In one embodiment, the second acidic monomeric units each independently comprise, per monomeric unit, at least one group according to structure (B.I):

$$—R^{32}—R^{31} \tag{B.I}$$

wherein
$R^{31}$ is a moiety that comprises at least one carboxylic acid, sulfonic acid, or phosphoric acid group, and
$R^{32}$ is absent or is a bivalent linking group.

In one embodiment, $R^{32}$ is O, —(CH₂)ₙ—O—, or is according to structure (structure (B.II):

$$\underset{\underset{\|}{C}}{O}—A— \tag{B.II}$$

wherein:
n is an integer of from 1 to 6,
A is O or NR¹⁷, and
R¹⁷ is H or (C₁-C₄)alkyl.

In one embodiment, the second acidic monomeric units each independently comprise one or two carboxy groups per monomeric unit and may, if the second acidic monomeric unit comprises a single carboxy group, further comprise an ester group according to —CH₂COOR³³, wherein R³³ is alkyl, more typically, (C₁-C₆)alkyl.

The second acidic monomeric units may be made by known synthetic techniques, such as, for example, by grafting of one or more groups according to structure (B.I) onto a polymer backbone, such as a hydrocarbon polymer backbone, a polyester polymer backbone, or a polysaccharide polymer backbone. In the alternative, they may be made by polymerizing a monomer that comprises a reactive functional group and at least one group according to structure (B.I) per molecule.

In one embodiment, the second acidic monomeric units are derived from polymerizing a monomer comprising a reactive functional group and a group according to structure (B.XXI) per molecule.

In one embodiment, the reactive functional group is an ethylenically unsaturated group so the monomer comprising a reactive functional group is an ethylenically unsaturated monomer. As a result the second acidic monomer comprises at least one site of ethylenic unsaturation, more typically, an α-, β-unsaturated carbonyl moiety, and at least one group according to structure (B.XXI) per molecule and is copolymerizable with the first acidic monomer and the nonionic monomer and the hydrophobic monomer.

In one embodiment the second acidic monomer comprises one or more ethylenically unsaturated monocarboxylic acid monomers according to structure (B.III):

$$R^{34}—R^{32}—R^{31} \tag{B.III}$$

wherein:
$R^{31}$ and $R^{32}$ are each as described above, and
$R^{34}$ is a moiety having a site of ethylenic unsaturation.

In one embodiment, the compound according to structure (B.XXII) is an α-, β-unsaturated carbonyl compound. In one embodiment, R³⁴ is according to structure (B.IV):

$$CH_2\!=\!\underset{R^{19}}{\overset{}{C}}— \tag{B.IV}$$

wherein R¹⁹ is H or (C₁-C₄)alkyl.

Suitable second acidic monomers include, for example, ethylenically unsaturated carboxylic acid monomers, such as acrylic acid and methacrylic acid, ethylenically unsaturated dicarboxylic acid monomers, such as maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups. The preferred second acidic monomeric units are derived from one or more monomers selected from acrylic acid, methacrylic acid, and mixtures thereof. Methacrylic acid has the following formula B.V:

B.V $$\text{H}_2\text{C}=\underset{\text{CH}_3}{\text{C}}-\text{C}(=\text{O})\text{OH}$$

C. Nonionic Monomeric Units for ASE and/or HASE Copolymer

In one embodiment, the polymer of the present invention further comprises one or more nonionic monomeric units.

In one embodiment, the nonionic monomeric units each independently comprise, per monomeric unit, at least one group according to structure (C.I):

$$—R^{42}—R^{41} \quad (C.I)$$

wherein
$R^{41}$ is alkyl, hydroxyalkyl, alkoxyalkyl, cycloalkyl, aryl, arylalkyl, or aryloxy, and
$R^{42}$ is absent or is a bivalent linking group.

In one embodiment, $R^{41}$ is $(C_1-C_{22})$alkyl, $(C_1-C_{22})$hydroxyalkyl, $(O_2—C_{22})$alkoxyalkyl, $(C_6-C_{24})$cycloalkyl, $(C_6-C_{40})$aryl, or $(C_7-C_{40})$aryl alkyl, more typically $(O_2—C_{1-2})$alkyl.

In one embodiment, $R^{41}$ is $(C_1-C_{22})$alkyl, more typically, $(C_1-C_{12})$alkyl.

In one embodiment, $R^{42}$ is O, $—(CH_2)_n—O—$, wherein n is an integer of from 1 to 6, or is according to structure (C.II):

$$—\underset{\substack{\|\\O}}{C}—A— \quad (C.II)$$

wherein:
n is an integer of from 1 to 6,
A is O or $NR^{17}$, and
$R^{17}$ is H or $(C_1-C_4)$alkyl.

The nonionic monomeric units may be made by known synthetic techniques, such as, for example, by grafting of one or more groups according to structure (C.XXIII) onto a polymer backbone, such as a hydrocarbon polymer backbone, a polyester polymer backbone, or a polysaccharide polymer backbone, or a backbone made by polymerization, with, for example, the above described first acidic, second acidic, and hydrophobic monomers, of at least one other monomer selected from monomers that comprise a reactive functional group and at least one group according to structure (C.XXIII) per molecule and copolymerizable with the first, second, and third monomers. Alternatively, the nonionic monomeric units may simply be non-grafted portions of a polymer backbone.

In one embodiment, the nonionic monomeric units are derived from a nonionic monomer, for example, ethyl acrylate, that comprises a reactive functional group and a group according to structure (C.XXIII), and is copolymerizable with the first acidic monomers, second acidic monomers and hydrophobic monomers.

In one embodiment, the reactive functional group of the nonionic monomer is an ethylenically unsaturated group and the nonionic monomer is an ethylenically unsaturated monomer comprising at least one site of ethylenic unsaturation, more typically, an α-, β-unsaturated carbonyl moiety and at least one group according to structure (C.XXIII) per molecule.

In one embodiment, the nonionic monomer comprises one or more compounds according to structure (C.III):

$$R^{43}—R^{42}—R^{41} \quad (C.III)$$

wherein:
$R^{41}$ and $R^{42}$ are each as described above, and
$R^{43}$ is a moiety having a site of ethylenic unsaturation.

In one embodiment, the compound according to structure (C.III) is an α-, β-unsaturated carbonyl compound. In one embodiment, $R^{43}$ is according to structure (C.IV):

$$CH_2=\underset{R^{19}}{C}— \quad (C.IV)$$

wherein $R^{19}$ is H or $(C_1-C_4)$alkyl.

Suitable nonionic monomers include unsaturated monomers containing at least one group according to structure C.XXIII per molecule, including (meth)acrylic esters such as: methyl(meth)acrylate, ethyl(meth)acrylate, butyl(meth)acrylate, isobutyl(meth)acrylate, cyclohexyl(meth)acrylate, 2-ethylhexyl(meth)acrylate, isodecyl(meth)acrylate, lauryl (meth)acrylate isobornyl(meth)acrylate, benzyl(meth)acrylate, hydroxyethyl(meth)acrylate, hydroxypropyl(meth)acrylate, methoxyethyl(meth)acrylate, ethoxyethyl(meth)acrylate, phenoxyethyl(meth)acrylate, tetrahydrofurfuryl (meth)acrylate, glycidyl(meth)acrylate, dimethylaminoethyl (meth)acrylate, diethylaminoethyl(meth)acrylate, tert-butylaminoethyl(meth)acrylate, and acetoxyethyl(meth)acrylate, (meth)acrylamides such as, (meth)acrylamide, N-methylol(meth)acrylamide, N-butoxyethyl(meth)acrylamide, N,N-dimethyl(meth)acrylamide, N-isopropyl(meth)acrylamide, N-tert-butyl(meth)acrylamide,N-tert-octyl (meth)acrylamide, and diacetone(meth)acrylamide, vinyl esters such as vinyl acetate, vinyl propionate, vinyl 2-ethylhexanoate, N-vinylamides such as: N-vinylpyrrolidone, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the HASE copolymer of the present invention is crosslinked. A crosslinked polymer can be made by, for example, reacting a mixture of hydrophobic, first acidic, and second acidic monomers with a nonionic monomer having more than one reactive functional group, such as for example, more than one site of ethylenic unsaturation per molecule. In one embodiment, the nonionic monomer comprises least one monomeric compound having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof.

Ethylene glycol dimethylacrylate has the following formula C.IV.

C.IV

In one embodiment, the polymer of the present invention comprises nonionic units derived from one or more ($C_1$-$C_{22}$) alkyl(meth)acrylic esters, more typically ($C_1$-$C_{12}$)alkyl (meth)acrylic esters, such as ethyl acrylate, butyl methacrylate, or ethylhexyl acrylate.

D. Hydrophobic Monomers for HASE Copolymer

In contrast to the ASE copolymers, the HASE copolymers further comprise hydrophobic monomeric units derived from a hydrophobic monomer. These hydrophobic monomers are ethylenically unsaturated hydrophobic monomers.

Preferably, the hydrophobic monomeric units each independently comprise, per monomeric unit, at least one branched ($C_5$-$C_{50}$)alkyl or bicycloheptyl-polyether or bicycloheptenyl-polyether group according to structure (D.I):

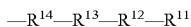 (D.I).

In one embodiment, $R^{11}$ is bicyclo[d.e.f]heptyl or bicyclo[d.e.f]heptenyl, wherein d is 2, 3, or 4, e is 1 or 2, f is 0 or 1, and the sum of d+e+f=5, and wherein the bicyclo[d.e.f]heptyl or bicyclo[d.e.f]heptenyl may, optionally, be substituted on one or more of the ring carbon atoms by one or more ($C_1$-$C_6$) alkyl groups, $R^{12}$ is absent or is a bivalent linking group,
$R^{13}$ is bivalent polyether group, and
$R^{14}$ is absent or is a bivalent linking group.

Suitable bicycloheptyl- and bicycloheptenyl-moieties may be derived from, for example, terpenic compounds having core (non-substituted) 7 carbon atom bicyclic ring systems according to structures (D.II)-(D.VI):

 (D.II) [2.2.1]

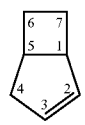 (D.III) [3.2.0]

 (D.IV.a) [3.1.1]

 (D.IV) [3.1.1]

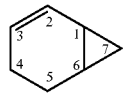 (D.V) [4.1.0]

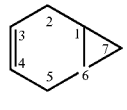 (D.VI) [4.1.0]

More typically, $R^{11}$ is:

a bicyclo[2.2.1]heptyl or bicyclo[2.2.1]heptenyl group bonded to $R^2$, if present, or to $R^3$, if $R^2$ is not present, via its carbon atom at the 2-position or 3-position and is typically substituted on its carbon atom at the 7 position by one or two ($C_1$-$C_6$)alkyl radicals, more typically by two methyl radicals, or a bicyclo[3.1.1]heptyl or bicyclo[3.1.1]heptenyl group bonded to $R^2$, if present, or to $R^3$, if $R^2$ is not present, via its carbon atom at the 2-position or 3-position and is typically substituted on its carbon atom at the 6-position or 7-position by one or two ($C_1$-$C_6$)alkyl radicals, more typically by two methyl radicals.

In another embodiment, $R^{11}$ is branched ($C_5$-$C_{50}$) alkyl group, more typically a branched alkyl group according to structure (D.VIII):

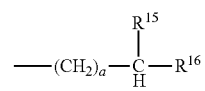 (D.VIII)

wherein:
$R^{15}$ and $R^{16}$ are each independently ($C_1$-$C_{48}$)alkyl, and
a is an integer of from 0 to 40,
provided that $R^{11}$, that is, $R^{15}$, $R^{16}$ and the —$(CH_2)_a$— radical taken together, comprises a total of from about 5 to about 50, more typically about 12 to about 50, carbon atoms;
$R^{12}$ is absent or is a bivalent linking group,
$R^{13}$ is bivalent polyether group, and
$R^{14}$ is absent or is a bivalent linking group.

More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (D.VIII):

—$(CH_2)_b$-A- (D.IX)

wherein A is O or absent, and b is an integer of from 1 to 6.

More typically, $R^{13}$ is a bivalent polyether group comprising a linear chain of from 2 to 100 units, each of which may independently be ($O_2$—$C_4$)oxyalkylene, more typically, ($C_2$-$C_3$)oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R^{13}$ is according to structure (D.X):

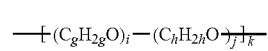 (D.X)

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

If i≠0, j≠0, and g≠h, the respective —($C_pH_{2p}O$)— and (—$C_qH_{2q}O$)— oxylakylene units may be arranged randomly, in blocks, or in alternating order.

In one embodiment,
g=2,
h=3, is an integer of from 1 to 50, more typically 10 to 40, and even more typically from 15 to about 30, j is an integer of from 1 to 30, more typically from 2 to 20, and even more typically from about 2 to about 10, and k=1.

In one embodiment, $R^{14}$ is O, $-(CH_2)_n-O-$, or is according to structure (D.XI):

$$\underset{\text{(D.XI)}}{-\overset{O}{\underset{\|}{C}}-A-}$$

wherein:
n is an integer of from 1 to 6,
A is O or $NR^{17}$, and
$R^{17}$ is H or $(C_1-C_4)$alkyl.

In another embodiment of structure (D.I) $R^{11}$ is a tri-styryl group according to the following structure D.XII.

D.XII

[structure showing benzene ring with R1, R2, R3 substituents]

wherein R1, R2 and R3 are independently selected from the following structures D.XIIa, D.XIIb, D.XIIc, D.XIId.

D.XIIIa
$-CH_2-\phi$ ,

D.XIIIb
$-CH_2-$[cyclohexyl],

D.XIIIc
$-\underset{CH_3}{\overset{|}{CH}}-\phi$ , or

D.XIIId
$-\underset{CH_3}{\overset{|}{CH}}-$[cyclohexyl].

The hydrophobic monomeric units may be made by known synthetic techniques, such as, for example, by grafting of one or more groups according to structure (D.I) onto a polymer backbone, such as a hydrocarbon polymer backbone, a polyester polymer backbone, or a polysaccharide polymer backbone, or by copolymerization, with, for example, the first acidic monomer, second acidic monomer and nonionic monomer monomer described above, of at least one other monomer selected from monomers that comprise a reactive functional group and at least one group according to structure (D.I) per molecule.

In one embodiment, the hydrophobic monomeric units are derived from at least one hydrophobic monomer selected from monomers that comprise a reactive functional group and at least one group according to structure (D.I) per molecule.

In one embodiment, the reactive functional group of the first monomer is an ethylenically unsaturated group. Thus, the hydrophobic monomer is selected from ethylenically unsaturated monomers that comprise at least one site of ethylenic unsaturation, more typically, an α-, β-unsaturated carbonyl moiety, and least one group according to structure (I) per molecule.

In one embodiment, the hydrophobic monomer comprises one or more compounds according to structure (D.XIV):

$$R^{18}-R^{14}-R^{13}-R^{12}-R^{11} \qquad \text{(D.XIV)}$$

wherein:
$R^{11}$, $R^{12}$, $R^{13}$ and $R^{14}$ are each as described above, and
$R^{18}$ is a moiety having a site of ethylenic unsaturation.

In one embodiment, the compound according to structure (D.XI) is an α-, β-unsaturated carbonyl compound.

In one embodiment, $R^{18}$ is according to structure (D.XV):

$$CH_2=\underset{R^{19}}{\overset{|}{C}}- \qquad \text{(D.XV)}$$

wherein $R^{19}$ is H or $(C_1-C_4)$alkyl.

In one embodiment, the hydrophobic monomer is selected from monomers according to structure (D.XVI):

$$CH_2=\underset{R^{19}}{\overset{|}{C}}-\overset{O}{\underset{\|}{C}}-O-[(C_gH_{2g}O)_i-(C_hH_{2h}O)_j]_k-(CH_2)_b-R^{11} \qquad \text{(D.XVI)}$$

wherein:
$R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups, or $R^{11}$ is a tri-styryl group according to the above-discussed structure D.XII.
and
$R^{19}$, b, g, h, i, j, and k are each as defined above, namely:
$R^{19}$ is H or $(C_1-C_4)$alkyl,
b is an integer of from 1 to 6,
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

Preferably $R^{11}$ is the bicyclo[d.e.f]heptyl or bicyclo[d.e.f]heptenyl group.

In another embodiment of monomers according to structure (D.XVI) $R^{11}$ is a tri-styryl group according to the following structure D.XII and $R^{19}$, b, g, h, i, j, and k are each as defined above. An example of a suitable monomer has structure D.XVIa:

D.XVIa

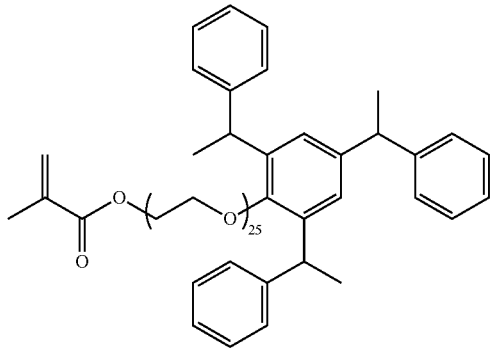

In one embodiment, the hydrophobic monomer comprises one or more compounds according to structure (D.XVII):

(D.XVII)

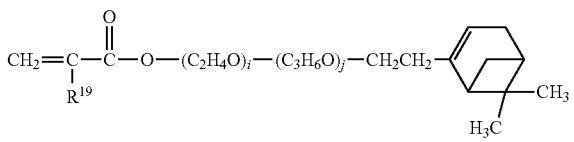

wherein i, j, and $R^{19}$ are each as described above, and, more typically, i is an integer of from 10 to 40, and even more typically from 15 to about 30, or from about 20 to about 30, and j is an integer of from 1 to 20, and even more typically from about 2 to about 10. A preferred version of this structure has the structure D.XVIIa:

D.XVIIa

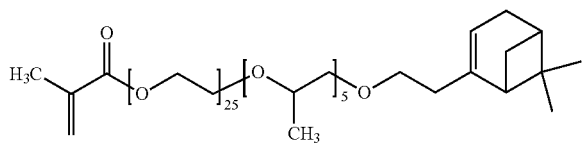

In another embodiment, the hydrophobic monomer comprises one or more compounds according to structure (D.XVIII):

(D.XVIII)

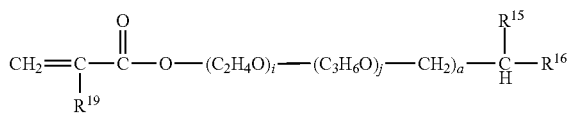

wherein a, i, j, and $R^{15}$, $R^{16}$, and $R^{19}$ are each as described above.

Suitable hydrophobic monomer may be made by known synthetic methods. For example, a bicycloheptenyl intermediate compound (D.XIX), known as "Nopol":

(D.XIX)

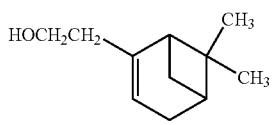

is made by reacting β-pinene with formaldehyde, and a bicycloheptyl intermediate compound (D.XX), known as "Arbanol":

(D.XX)

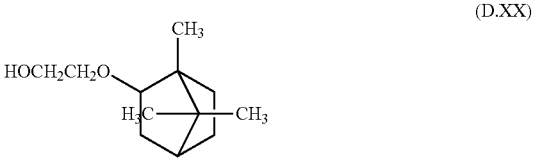

is made by isomerization of α-pinene to camphene and ethoxyhydroxylation of the camphene.

The bicycloheptyl- or bicycloheptenyl-intermediate may then be alkoxylated by reacting the bicycloheptyl- or bicycloheptenyl intermediate with one or more alkylene oxide compounds, such as ethylene oxide or propylene oxide, to form a bicycloheptyl-, or bicycloheptenyl-polyether intermediate. The alkoxylation may be conducted according to well known methods, typically at a temperature in the range of about 100° to about 250° C. and at a pressure in the range of from about 1 to about 4 bars, in the presence of a catalyst, such as a strong base, an aliphatic amine, or a Lewis acid, and an inert gas, such as nitrogen or argon.

The bicycloheptyl-, or bicycloheptenyl-polyether monomer may then be formed from the bicycloheptyl- or bicycloheptenyl-polyether intermediate by addition of a moiety containing an ethylenically unsaturated group to the bicycloheptyl- or bicycloheptenyl-polyether intermediate, by, for example, esterification, under suitable reaction conditions, of the bicycloheptyl- or bicycloheptenyl-polyether intermediate with, for example, methacrylic anhydride.

Alternatively, a monomer comprising a ethylenically unsaturated group, such as for example, a polyethylene glycol monomethacrylate, which may optionally be further alkoxylated, may be reacted with the bicycloheptyl- or bicycloheptenyl-intermediate to form the bicycloheptyl-, or bicycloheptenyl-polyether monomer.

In another embodiment, the hydrophobic monomeric units each independently comprise, per monomeric unit, at least one group according to structure (D.XXI):

$$R^{23}-R^{22}-R^{21} \quad \text{(D.XXI)}$$

wherein:
$R^{21}$ is linear or branched $(C_5\text{-}C_{50})$alkyl, hydroxyalkyl, alkoxyalkyl, aryl, or aryalkyl,
$R^{22}$ is a bivalent polyether group,
$R^{23}$ is absent or is a bivalent linking group.

In one embodiment, $R^{21}$ is linear or branched $(C_5\text{-}C_{40})$ alkyl, more typically linear or branched $(C_{10}\text{-}C_{40})$alkyl, even more typically, linear or branched $(C_{16}\text{-}C_{40})$alkyl, and still more typically linear or branched $(C_{16}\text{-}C_{30})$alkyl. In one embodiment, $R^{21}$ is tridecyl, tetradecyl, pentadecyl, hexadecyl, heptadecyl, octadecyl, nonadecyl, eicosyl, heneicosyl, behenyl, tricosyl, tetracosyl, pentacosyl, hexacosyl, heptacosyl, octacosyl, nonacosyl, triacontyl, dotriacontyl, tritriacontyl, tetratriacontyl, pentatriacontyl, hexatriacontyl, heptatriacontyl, octatriacontyl, nonatriacontyl, or tetracontyl, more typically, hexadecyl, heptadecyl, octadecyl, nonadecyl, eicosyl, or behenyl.

In embodiment $R^{21}$ is hydroxyalkyl, such as, for example, hydroxyhexadecyl, hydroxyoctadecyl, or hydroxyeicosyl, or alkoxyalkyl, such as for example, methoxyhexadecyl, methoxyoctadecyl, or methoxyeicosyl.

In embodiment $R^{21}$ is aryl, such as, for example, phenyl, methylphenyl, methoxyphenyl, dibutylphenyl, triisobutylphenyl, or tristyrylphenyl, or arylalkyl, such as phenylmethyl, phenylethyl, or triphenylmethyl.

In one embodiment, the hydrophobic monomeric units each independently comprise at least one group according to structure (D.XVIII) (D.XXI) above wherein $R^{21}$ is a linear $(C_5\text{-}C_{50})$alkyl group.

In one embodiment, the hydrophobic monomeric units each independently comprise at least one group according to structure (D.XXI) above wherein $R^{21}$ is a branched $(C_5-C_{50})$ alkyl group, more typically a branched $(C_5-C_{50})$alkyl group according to structure (D.IX).

In one embodiment, the hydrophobic monomeric units comprise a mixture of hydrophobic monomeric units that each independently comprise at least one group according to structure (D.XXI) above wherein $R^{21}$ is a linear $(C_5-C_{50})$alkyl group and other hydrophobic monomeric units that each independently comprise at least one group according to structure (D.XXI) above wherein $R^{21}$ is a branched $(C_5-C_{50})$alkyl group, more typically a branched $(C_5-C_{50})$alkyl group according to structure (D.VIII) above.

In one embodiment, $R^{22}$ is a bivalent polyether group comprising a linear chain of from 2 to 100 units, each of which may independently be $(O_2-C_4)$oxyalkylene, more typically, $(C_2-C_3)$oxyalkylene. In one embodiment, $R^{22}$ is a bivalent polyether group comprising a chain of from 2 to 100 polymerized oxyethylene units.

In one embodiment, $R^{22}$ is according to structure (D.XXII):

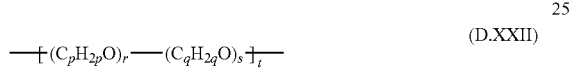
(D.XXII)

wherein:
p and q are independently integers of from 2 to 5, more typically 2 or 3,
each r is independently an integer of from 1 to about 80, more typically from 1 to about 50,
each s is independently an integer of from 0 to about 80, more typically from 0 to about 50,
t is an integer of from 1 to about 50, provided that the product obtained by multiplying the integer t times the sum of r+s is from 2 to about 100.

If r≠0, s≠0, and p≠q, the respective $-(C_pH_{2p}O)-$ and $-(C_qH_{2q}O)-$ oxylakylene units may be arranged randomly, in blocks, or in alternating order.

In one embodiment,
p=2,
q=3,
r is an integer of from 1 to 50, more typically 5 to 45, and even more typically from 10 to about 40,
s is an integer of from 1 to 30, more typically from 2 to 20, and even more typically from about 2 to about 10, and
t=1

In another embodiment,
p=2,
r is an integer of from 1 to 50, more typically 5 to 45, and even more typically from 10 to about 40,
s is 0, and
t=1.

In one embodiment, $R^{23}$ is O, $-(CH_2)_n-O-$ wherein n is an integer of from 1 to 6, or is according to structure (D.X) above, wherein A is O or $NR^{17}$, and $R^{17}$ is H or $(C_1-C_4)$alkyl.

The hydrophobic monomeric units may be made by known synthetic techniques, for example, by grafting of one or more groups according to structure D.XVII onto a polymer backbone, such as a hydrocarbon polymer backbone, a polyester polymer backbone, or a polysaccharide polymer backbone, or by copolymerization, with, for example, the above-described first acidic monomer, second acidic monomer and the nonionic monomer described above.

In one embodiment, the hydrophobic monomeric units are derived from copolymerizing at least one monomer that comprises a reactive functional group and at least one group according to structure (D.XXI) per molecule.

In one embodiment, the reactive group of the hydrophobic monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (D.XXI) per molecule and copolymerizable with the first monomer.

In one embodiment, the hydrophobic monomer comprises one or more compounds according to structure (D.XXIII):

$$R^{24}-R^{23}-R^{22}-R^{21} \quad \text{(D.XXIII)}$$

wherein:
$R^{21}$, $R^{22}$, and $R^{23}$ are each as described above, and
$R^{24}$ is a moiety having a site of ethylenic unsaturation. Thus the resulting hydrophobic monomeric unit has the structure (D.XXIV):

(D.XXIV)

In one embodiment, the compound according to structure (D.XIX) is an α-, β-unsaturated carbonyl compound. In one embodiment, $R^{23}$ is according to structure (D.X).

In one embodiment, the hydrophobic monomer comprises one or more compounds according to structure (D.XXV):

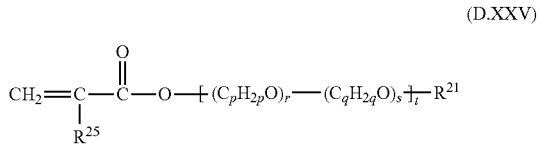
(D.XXV)

wherein
$R^{21}$ is linear or branched $(C_5-C_{50})$alkyl, hydroxyalkyl, alkoxyalkyl, aryl, or arylalkyl,
$R^{25}$ is methyl or ethyl, and
p and q are independently integers of from 2 to 5, more typically 2 or 3,
each r is independently an integer of from 1 to about 80, more typically from 1 to about 50,
each s is independently an integer of from 0 to about 80, more typically from 0 to about 50,
t is an integer of from 1 to about 50, provided that the product obtained by multiplying the integer t times the sum of r+s is from 2 to about 100; or p, q, r, s, and t are each as otherwise described above.

In one embodiment, the hydrophobic monomer comprises one or more compounds according to structure (D.XXV) wherein $R^{21}$ is linear $(C_{16}-C_{22})$alkyl.

In one embodiment, the hydrophobic monomer comprises one or more compounds according to structure (D.XXV) wherein $R^{21}$ is a branched $(C_5-C_{50})$alkyl group, more typically a branched $(C_5-C_{50})$alkyl group according to structure (D.VII) above. For example $R^{21}$ may have the structure D.XXVI

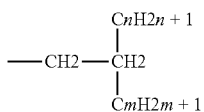
D.XXVI wherein m and n each, independently, are positive integers from 1 to 39 and m+n represents an integer from 4 to 40, as disclosed by US Patent Application Publication 2006/02700563 A1 to Yang et al, incorporated herein by reference.

In one embodiment, the hydrophobic monomer comprises one or more compounds according to structure (D.XX) wherein p=2, s=0, and t=1.

In one embodiment, the hydrophobic monomer comprises one or more compounds according to structure (D.XX) wherein $R^{21}$ is linear ($C_{16}$-$C_{22}$)alkyl, $R^{25}$ is methyl or ethyl, p=2, s=0, and t=1.

Suitable ethylenically unsaturated hydrophobic monomers include:

alkyl-polyether(meth)acrylates that comprise at least one linear or branched ($C_5$-$C_{40}$)alkyl-polyether group per molecule, such as hexyl polyalkoxylated(meth)acrylates, tridecyl polyalkoxylated(meth)acrylates, myristyl polyalkoxylated (meth)acrylates, cetyl polyalkoxylated(meth)acrylates, stearyl polyalkoxylated(methyl)acrylates, eicosyl polyalkoxylated(meth)acrylates, behenyl polyalkoxylated(meth)acrylates, melissyl polyalkoxylated(meth)acrylates, tristyrylphenoxyl polyalkoxylated(meth)acrylates, and mixtures thereof, alkyl-polyether(meth)acrylamides that comprise at least one ($C_5$-$C_{40}$)alkyl-polyether substituent group per molecule, such as hexyl polyalkoxylated(meth)acrylamides, tridecyl polyalkoxylated(meth)acrylamides, myristyl polyalkoxylated(meth)acrylamides, cetyl polyalkoxylated(meth)acrylamides, stearyl polyalkoxylated(methyl) acrylamides, eicosyl polyalkoxylated(meth)acrylamides, behenyl polyalkoxylated(meth)acrylamides, melissyl polyalkoxylated(meth)acrylamides and mixtures thereof, alkyl-polyether vinyl esters, alkyl-polyether vinyl ethers, or alkyl-polyether vinyl amides that comprise at least one ($C_5$-$C_{40}$)alkyl-polyether substituent group per molecule such as vinyl stearate polyalkoxylate, myristyl polyalkoxylated vinyl ether, and mixtures thereof, as well as mixtures of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and/or alkyl-polyether vinyl amides.

In one embodiment, the hydrophobic monomer comprises one or more alkyl-polyalkoxylated(meth)acrylates that comprise one linear or branched ($C_5$-$C_{40}$)alkyl-polyethoxylated group, more typically ($C_{10}$-$C_{22}$)alkyl-polyethoxylated group per molecule, such as decyl-polyethoxylated(meth)acrylates, tridecyl-polyethoxylated(meth)acrylates, myristyl-polyethoxylated(meth)acrylates, cetyl-polyethoxylated(meth) acrylates, stearyl-polyethoxylated(methyl)acrylates, eicosyl-polyethoxylated(meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

In one embodiment wherein the nonionic ethylenically unsaturated hydrophobic monomer comprises a compound according to structure a structure selected from the group consisting of structure D.XXVIIa and structure D.XXVIIb:

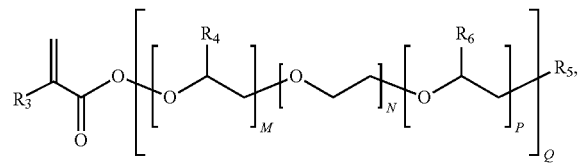
D.XXVIIa

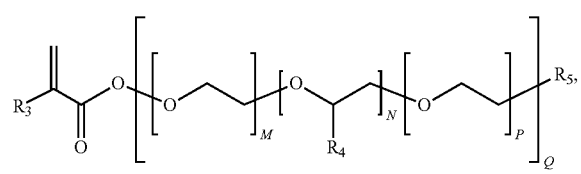
D.XXVIIb wherein $R_3$ is H or $CH_3$; $R_4$ is independently an alkyl chain containing 1 to about 4 carbon atoms; $R_5$ is an alkyl chain containing 1 to about 6 carbon atoms (preferably methyl); $R_6$ is an alkyl chain containing 1 to about 4 carbon atoms; M is an integer from 0 to about 50 (preferably about 1 to 50, more preferably about 5 to 30); N is an integer from 0 to 20 (preferably 1 to 20, more preferably 5 to 15); P is an integer from 0 to about 50 (preferably 0 to 30); wherein P+M is greater than or equal to 1; wherein Q is an integer from 1 to 4 (typically 1 to 2).

Some typical hydrophobic monomers have any of the structures D.XXVIII, D.XXIX, D.XXX, or D.XXXI,

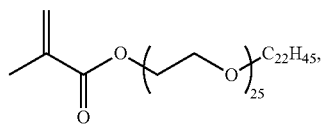
D.XXVIII

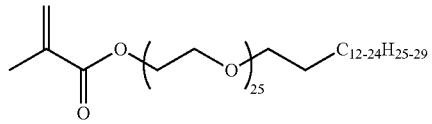
D.XXIX

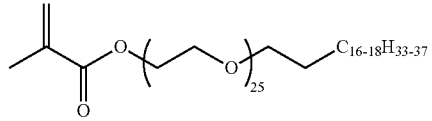
D.XXX

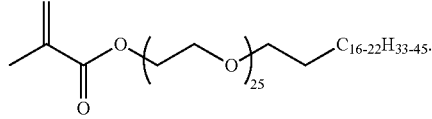
D.XXXI

III. Making the ASE and/or HASE Copolymer

The pH responsive ASE copolymer is the product of copolymerization of a mixture of monomers, comprising:

A. about 0.1-70 weight percent, typically 0.5-50, 0.7-40, 1-40, 5-40, 5-30 or 10 to 40 weight percent of at least one alpha beta-ethylenically unsaturated first acid monomer selected from the group consisting of mono-[2-(methacryloyloxy)ethyl]phthalate (also known as 2-(2-carboxybenzoyloxy)ethyl methacrylate, MAEP) and mono-[2-(Methacryloyloxy)ethyl hexahydro]phthalate (MAHP), B. about 0-45 weight percent, preferably 5 to 30 weight percent, of at least one C3-C8 alpha beta-ethylenically unsaturated acidic monomer, preferably a C3-C8 alpha beta-ethylenically unsaturated carboxylic acid monomer;

C. about 15-70 weight percent, typically 20 to 50 weight percent, of at least one non-ionic, copolymerizable C2-C12 alpha, beta-ethylenically unsaturated monomer.

The pH responsive HASE copolymer is the product of copolymerization of a mixture of monomers, comprising:

A. about 0.1-70 weight percent, typically 0.5-50, 0.7-40, 1-40, 5-40, 5-30 or 10 to 40 weight percent of at least one alpha beta-ethylenically unsaturated first acid monomer selected from the group consisting of mono-[2-(methacryloyloxy)ethyl]phthalate (also known as 2-(2-carboxybenzoyloxy)ethyl methacrylate, MAEP) and mono-[2-(Methacryloyloxy)ethyl hexahydro]phthalate (MAHP), B. about 0-45 weight percent, preferably 5 to 30 weight percent, of at least one C3-C8 alpha beta-ethylenically unsaturated acidic monomer, preferably a C3-C8 alpha beta-ethylenically unsaturated carboxylic acid monomer;

C. about 15-70 weight percent, typically 20 to 50 weight percent, of at least one non-ionic, copolymerizable C2-C12 alpha, beta-ethylenically unsaturated monomer; and D. about 0 to 30 weight percent, preferably 0.05 to 30 weight percent or typically 5 to 20 weight percent, of at least one non-ionic ethylenically unsaturated hydrophobic monomer.

In one embodiment, the pH responsive copolymer of the present invention is the product of polymerization of a mixture of monomers comprising, based on the 100 pbw of the total amount of the monomers:

(a) from about 0.1, more typically from about 1 or 5 pbw of the first acidic monomers, to about 70, more typically to about 40 pbw, of the one or more first acidic monomers, (b) from about 0, more typically from about 1, and even more typically from about 5, pbw of the second acidic monomers, to about 45, more typically to about 35, and even more typically to about 30, pbw of the one or more second acidic monomers, and (c) from about 15, more typically from about 20 pbw of the one or more nonionic acidic monomers, to about 70, more typically to about 50 pbw, of the one or more nonionic monomers, and (d) from about 0, more typically from about 0.05, even more typically from about 1, and still more typically from about 5, pbw of the one or more hydrophobic monomers, to about 30, more typically to about 25, and even more typically to about 20, pbw of the one or more hydrophobic monomers.

The pH responsive copolymer of the present invention can be conveniently prepared from the above-described monomers by known aqueous emulsion polymerization techniques using free-radical producing initiators, typically in an amount from 0.01 percent to 3 percent, based on the weight of the monomers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical producing initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature between about 60° C. and 90° C., but higher or lower temperatures may be used. The polymerization can be conducted batchwise, stepwise, or continuously with batch and/or continuous addition of the monomers, in a conventional manner.

The monomers can be copolymerized in such proportions, and the resulting emulsion polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. One or more fourth monomers may be added to adjust the properties of the polymer.

These polymeric products prepared by emulsion polymerization at an acid pH are in the form of stable aqueous colloidal dispersions containing the polymer dispersed as discrete particles having average particle diameters of about 400 to about 3000 Å (40 to 300 nanometers) and preferably about 600 to about 1750 Å (60 to 175 nanometers), as measured by light scattering. Dispersions containing polymer particles smaller than about 400 Å (40 nanometers) are difficult to stabilize, while particles larger than about 3000 Å (300 nanometers) reduce the ease of dispersion in the aqueous products to be thickened.

In one embodiment, the polymer composition is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively this (co)polymerization may also be conducted by different methods or in different solvents. The scope of methods and solvents is well known to those skilled in the art.

Thus, these polymers for use in the present invention can be made using known solution polymerization techniques, wherein the reactant monomers and initiator are dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The polymer product can be isolated through normal separation techniques, including solvent stripping.

In one embodiment, these polymers for use in the present invention exhibit a weight average molecular weight, as determined by gel permeation chromatography and light scattering of a solution of the polymer in tetrahydrofuran and compared to a polystyrene standard, of greater than or equal to 30,000 grams per mole ("g/mole"). HASE thickeners may not fully dissolve in THF but after hydrolysis they can dissolve in water and measurement can be run in a water gel permeation chromatography (GPC). Reference: Macromolecules 2000, 33, 2480. For example in a range of 30,000 to 5,000,000 g/mole. More typically the polymer of the present invention exhibits a weight average molecular weight of from about 100,000 g/mole, and even more typically from about 150,000 g/mole, to about 1,500,000 g/mole, more typically to about 1,000,000 g/mole, and even more typically to about 800,000 g/mole.

In one embodiment, these pH responsive copolymers for use in the present invention are in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 1.5 to about 3. When thickening of the composition is desired, the pH of the composition can be increased to a value above about 5 by addition of a base to solubilize the polymer.

These ASE and HASE copolymers and compositions for use as thickeners in the present invention are pH-responsive. At the lower pH levels at which the emulsion polymerization takes place, i.e., pH levels of 5 or less, the composition is relatively thin or non-viscous. When the pH of the copolymer dispersion is neutralized or adjusted by addition of a base to a pH of about 5.5 or more, preferably about 6 to about 11, the composition thickens substantially. The composition turns from semi-opaque or opaque to translucent or transparent as viscosity increases. Viscosity increases as copolymer dissolves partially or completely in the aqueous phase of the composition. Neutralization can occur in situ when the emulsion copolymer is blended with the base and added to the aqueous phase. Or, if desired for a given application, neutralization can be carried out when blending with an aqueous product. Useful bases include, but are not limited to, ammonium hydroxide, an amine, sodium hydroxide, potassium carbonate or the like.

For example, the HASE copolymer having a polymer backbone including MAA and EA is a pH-sensitive thickener. Typically the copolymer is a latex at pH=2.3. When neutralized with a suitable base to a pH above about 5.5, the carboxyl groups on the methacrylic acid ionize to carboxylate ions. The charge on the polymer induces a conformational change, and the white latex becomes water-soluble, thus increasing the hydrodynamic volume of the polymer. When the HASE copolymers swell, the pendant hydrophobic groups are free to build associations with one another and with other hydrophobes available in the formulation, such as surfactants, particulates, emulsion droplets and dyes. This phenomenon creates a network structure that results in a significant viscosity build.

IV. Uses of the pH Responsive Polymer

The polymers and polymer compositions according to the present invention are useful as water-soluble thickeners for a wide variety of applications ranging from home care, personal care and oilfield drilling fluids. They are particularly useful for aqueous paints and coatings. Solution-polymerized polymers can be used in solvent systems or emulsified by known techniques for use in aqueous systems. Other uses include latexes and detergents. Useful cosmetic compositions will typically have an aqueous carrier, a pigment and/or cosmetic active, a HASE emulsion polymer, and optional adjuvants. Useful detergents and cleansers will typically have aqueous carrier, a HASE emulsion polymer, and optional adjuvants. Oilfield drilling fluids will typically have an aqueous carrier, HASE emulsion polymer as a thickener/viscosity modifier, and optional adjuvants. The oilfield drilling fluids are injected into the oilfield formation. Useful latex coatings will typically have an aqueous carrier, a HASE emulsion polymer, and optional adjuvants.

The HASE emulsion polymers according to the present invention as described herein are particularly useful as thickeners for a wide variety of water-based compositions. Such compositions include brine, slurries, and colloidal dispersions of water-insoluble inorganic and organic materials, such as natural rubber, synthetic or artificial latexes. The emulsion polymers of the invention are especially useful in areas requiring thickening at neutral pHs, such as in cosmetics.

In one embodiment, the aqueous composition comprising the pH responsive polymer of the present invention exhibits viscoelastic properties at neutral to alkaline pH values, typically at pH values greater than or equal to about 5, more typically greater than or equal to about 5.5, even more typically from about 6 to about 9.

V. Use of the pH Responsive Polymer With Binders Which Are Latex Polymers

Embodiments of the invention, such as latex paint, may contain more than one category of latex. There can be a first latex namely, the HASE copolymer, as a thickener. There can also be a second latex, for example RHOPLEX SG30 or REVACRYL synthetic latex emulsion resins, as a binder for latex paint.

Synthetic latexes take the form of aqueous dispersions/suspensions of particles of latex polymers. Synthetic latexes include aqueous colloidal dispersions of water-insoluble polymers prepared by emulsion polymerization of one or more ethylenically unsaturated monomers. Typical of such synthetic latexes are emulsion copolymers of monoethylenically unsaturated compounds, such as styrene, methyl methacrylate, acrylonitrile with a conjugated diolefin, such as butadiene or isoprene; copolymers of styrene, acrylic and methacrylic esters, copolymers of vinyl halide, vinylidene halide, vinyl acetate and the like. Many other ethylenically unsaturated monomers or combinations thereof can be emulsion polymerized to form synthetic latexes. Such latexes are commonly employed in paints (latex paints) and coatings. The composition of the present invention may be added to latexes to modify/increase viscosity.

The polymeric thickeners of this invention are advantageous for use with the water-based compositions according to the foregoing description and with compositions containing those materials, especially coating compositions of various types. Mixtures or combinations of two or more thickeners may be used, if desired. Of course the latex polymers used in coating compositions are preferably film-forming at temperatures about 25 degrees C. or less, either inherently or through the use of plasticizers. Such coating compositions include water-based consumer and industrial paints; sizing, adhesives and other coatings for paper, paperboard, textiles; and the like.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

The polymer compositions of the present invention may be added to aqueous product systems at a wide range of amounts depending on the desired system properties and end use applications. In latex paints, the composition is added such that the emulsion (HASE) polymer according to the present invention is present at about 0.05 to about 5.0 weight percent and preferably about 0.1 to about 3.0 weight percent based on total weight of the latex paint, including all of its components, such as water, HASE polymer, latex polymer, pigment, and any adjuvants.

The present invention also includes a method of preparing an aqueous coating composition by mixing together at least one latex polymer derived from at least one monomer and blended with at least one pH responsive copolymer as described above, and at least one pigment. Preferably, the latex polymer is in the form of latex polymer dispersion. The additives discussed above can be added in any suitable order to the latex polymer, the pigment, or combinations thereof, to provide these additives in the aqueous coating composition. In the case of paint formulations, the aqueous coating composition preferably has a pH of from 7 to 10.

In formulating latexes and latex paints/coatings, physical properties that may be considered include, but are not limited to, viscosity versus shear rate, ease of application to surface, spreadability, and shear thinning.

VI. Emulsion Polymerization to Make Latex Binder for Latex Paint

Emulsion polymerization is discussed in G. Pohlein, "Emulsion Polymerization", Encyclopedia of Polymer Science and Engineering, vol. 6, pp. 1-51 (John Wiley & Sons, Inc., NY, N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The monomers typically employed in emulsion polymerization to make latex for latex paint include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof. This is further discussed below in the section entitled "Latex Monomers".

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like. Commonly used redox initiation systems are described e.g., by A. S. Sarac in Progress in Polymer Science 24 (1999), 1149-1204.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Emulsion polymerization occurs in the presence of an emulsifier. Typically the mixture contains 0.5 to 6 wt % emulsifier based on weight of latex monomers Typical emulsifiers are ionic or non-ionic surfactants polymerizable or non-polymerizable in the aqueous coating composition including latex polymer. Suitable ionic and nonionic surfactants are alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The polymer latex binder can be produced by first preparing an initiator solution comprising the initiator and water. A monomer pre-emulsion is also prepared comprising one or more surfactants (emulsifiers), and other latex monomers to be used to form the latex polymer, water, and additional additives such as NaOH.

Thus, a typical process of emulsion polymerization preferably involves charging water to a reactor and feeding as separate streams a pre-emulsion of the monomer and a solution of the initiator. In particular, the polymer latex binder can be prepared using emulsion polymerization by feeding the monomers used to form the latex binder to a reactor in the presence of at least one initiator and at least one surfactant and polymerizing the monomers to produce the latex binder. Typically the initiator solution and monomer pre-emulsion are continuously added to the reactor over a predetermined period of time (e.g. 1.5-5 hours) to cause polymerization of latex monomers to produce the latex polymer.

Prior to the addition of the initiator solution and the monomer pre-emulsion, a seed latex such as a polystyrene seed latex can be added to the reactor. For example, a small amount of the pre-emulsion and a portion of the initiator may be charged initially at the reaction temperature to produce "seed" latex. The "seed" latex procedure results in better particle-size reproducibility.

Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, namely initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

The reactor is operated at desired reaction temperature at least until all the monomers are fed to produce the polymer latex binder. Once the polymer latex binder is prepared, it is preferably chemically stripped thereby decreasing its residual monomer content. Preferably, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24 (1999), 1149-1204, to the latex binder at an elevated temperature and for a predetermined period of time (e.g. 0.5 hours). The pH of the latex binder can then be adjusted and other additives added after the chemical stripping step.

In the above emulsions, the polymer preferably exists as a generally spherical particle, dispersed in water, with a diameter of about 50 nanometers to about 500 nanometers.

For purposes of this description, monomers from which latex polymers may be derived are termed "latex monomers".

The latex monomers fed to a reactor to prepare the polymer latex binder preferably include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, (alpha)-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR neo vinyl esters by ExxonMobil Chemical Company), itaconic acid, crotonic acid, maleic acid, fumaric acid, and ethylene. It is also possible to include C4-C8 conjugated dienes such as 1,3-butadiene, isoprene or chloroprene. Commonly used monomers in making acrylic paints are butyl acrylate, methyl methacrylate, ethyl acrylate and the like. Preferably, the monomers include one or more monomers selected from the group consisting of n-butyl acrylate, methyl methacrylate, styrene and 2-ethylhexyl acrylate.

The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In typical acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The latex polymer dispersion preferably includes from about 30 to about 75% solids and a mean latex particle size of from about 70 to about 650 nm. The latex polymer is preferably present in the aqueous coating composition in an amount from about 5 to about 60 percent by weight, and more preferably from about 8 to about 40 percent by weight (i.e. the weight percentage of the dry latex polymer based on the total weight of the coating composition).

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

VII. Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

VIII. Other Additives

As described above, latex paints and coatings may contain various adjuvants.

The aqueous coating compositions of the invention include less than 2% by weight and preferably less than 1.0% by weight of anti-freeze agents based on the total weight of the aqueous coating composition. For example, the aqueous coating compositions may be substantially free of anti-freeze agents.

The aqueous coating composition typically includes at least one pigment. The term "pigment" as used herein includes non-film-forming solids such as pigments, extenders, and fillers. The at least one pigment is preferably selected from the group consisting of TiO2 (in both anastase and rutile forms), clay (aluminum silicate), CaCO3 (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), and ATTAGELS (commercially available from Engelhard). More preferably, the at least one pigment includes TiO2, CaCO3 or clay. Generally, the mean particle sizes of the pigments range from about 0.01 to about 50 microns. For example, the TiO2 particles used in the aqueous coating composition typically have a mean particle size of from about 0.15 to about 0.40 microns. The pigment can be added to the aqueous coating composition as a powder or in slurry form. The pigment is preferably present in the aqueous coating composition in an amount from about 5 to about 50 percent by weight, more preferably from about 10 to about 40 percent by weight.

The coating composition can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, additional biocides, additional mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more preferably from about 1 to about 10% by weight based on the total weight of the coating composition.

The aqueous coating composition typically includes less than 10.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More preferably, the aqueous coating composition includes less than 5.0% or is substantially free (e.g. includes less than 0.1%) of anti-freeze agents. Accordingly, the aqueous coating composition of the invention preferably has a VOC level of less than about 100 g/L and more preferably less than or equal to about 50 g/L.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more preferably from about 35% to about 80% by weight water. Stated differently, the total solids content of the aqueous coating composition is typically from about 15% to about 90%, more preferably from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, additional biocides, additional mildewcides, colorants, waxes, and the like, that do not evaporate upon drying of the coating composition.

Biocides are substances that kill or inhibit the growth of microorganisms such as bacteria, fungi and algae. Biocides include chlorinated hydrocarbons, organometallics, halogen-releasing compounds, metallic salts, quaternary ammonium compounds, phenolics and organic sulfur compounds.

Exemplary of organic sulfur compounds are compounds based on an isothiazolinone or isothiazolothione structure. The biocidal activity of these compounds is effected by inactivation of essential enzymes of microbial metabolism which require sulfhydryl groups for activity. These enzymes include phosphoenolpyruvate transphosphorase and a number of dehydrogenases. The thio moiety of the isothiazolinone or isothiazolothione compounds reacts with the free sulfhydryl groups of an enzyme to form a disulfide bond between the enzyme molecule and the isothiazolinone or isothiazolothione molecule rendering the sulfhydryl unavailable for interaction with substrate or effector molecules.

Isothiazolinone and isothiazolothione biocides have found widespread use as latex preservatives. Most latex emulsions are water based and are prone to microbial attack. Biocides are typically added to the finished latex after all processing is completed to protect the latex from microbial attack. The present compositions and methods may also include Isothiazolinone biocides. Biocides which are widely used as latex preservatives include PROXEL GXL, having an active ingredient of 1,2-benzisothiazolin-3-one (BIT), PROMEXAL W50, having an active ingredient of 2-methyl-4,5-trimethylene-4-isothiazolin-3-one, and KATHON LX, a blend of 5-chloro-2-methyl-4-isothiazolin-3-one and 2-methyl-4-isothiazolin-3-one active ingredients.

Typical isothiazolinones or isothiazolothiones are represented by the general formula (I):

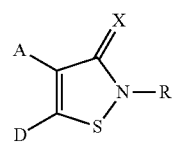

or a salt or a complex thereof;

wherein X is oxygen or sulfur; R is hydrogen, a substituted or unsubstituted hydrocarbyl group, a substituted or unsubstituted hydrocarbylthio group, a substituted or unsubstituted hydrocarbyloxy group or a carbamoyl group; and each of A and D is independently hydrogen, a halogen atom, a cyano group, a substituted or unsubstituted hydrocarbyl group or a direct bond to the other of A or D.

When R, A and D are, or contain, substituted hydrocarbyl groups, the substituents are preferably independently halogen, alkoxy or alkylthio where the alkyl groups contain 1 to 4 carbon atoms. If R is a carbamoyl group, preferably it is of the general type —CON(H)($R^1$) where $R^1$ is a hydrogen atom or a hydrocarbyl group, which may be substituted with halogen, alkoxy or alkylthio substituents. It is generally preferred that R is a hydrogen atom or a lower alkyl group of 1 to 4 carbon atoms. Most preferably, R is hydrogen or a methyl group.

Preferably, A and D, together with the carbon atoms to which they are attached, form a five- or six-membered substituted or unsubstituted ring. The ring substituents are preferably halogen, alkyl of 1 to 4 carbon atoms, alkoxy of 1 to 4 carbon atoms or alkylthio of 1 to 4 carbon atoms. The ring may contain a heteroatom such as a nitrogen atom replacing a carbon atom. Most preferably, A and D form a hydrocarbon ring such as benzene, cyclopentene or cyclohexene.

Alternatively, A and D are separate groups. Preferably, at least one of A and D is not a hydrogen atom and most preferably, at least one of A and D is a halogen atom or an alkyl group of 1 to 4 carbon atoms.

The biocidal isothiazolinone compounds include 5-chloro-2-methyl-4-isothiazolin-3-one (where R is methyl, A is hydrogen and D is chlorine); 2-methyl-4-isothiazolin-3-one (where R is methyl and A and D are both hydrogen); 4,5-dichloro-2-methylisothiazolin-3-one (where R is methyl and A and D are both chlorine); 2-n-octylisothiazolin-3-one (where R is n-octyl and A and D are both hydrogen; 1,2-benzisothiazolin-3-one (where R is hydrogen and A and D, together with the carbon atoms to which they are attached, form a benzene ring); 4,5-trimethylene-4-isothiazolin-3-one (where R is hydrogen and A and D, together with the carbon atoms to which they are attached, form a cyclopentene ring) and 2-methyl-4,5-trimethylene-4-isothiazolin-3-one (where R is methyl and A and D, together with the carbon atoms to which they are attached, form a cyclopentene ring).

A typical the biocidal compound of this family which may be used as the additional biocidal compound in the present invention is one where R is hydrogen and A and D together form an unsubstituted 5- or 6-membered hydrocarbon ring as in the compounds 1,2-benzisothiazolin-3-one and 4,5-trimethylene-4-isothiazol in-3-one.

Certain of the isothiazolinone or isothiazolothione compounds which may be used as the additional biocidal compound can have improved solubility in water when ill the form of a salt or complex. The salt or complex may be with any suitable cation such as an amine (including an alkanolamine) or a metal. Preferably, any metal salt or complex contains a monovalent metal such as an alkali metal. The alkali metal may be lithium, sodium or potassium. Most preferably, the alkali metal salt is a sodium salt in view of the ready availability of suitable sodium compounds from which to prepare the salt.

Certain isothiazolinone or isothiazolothione compounds useful as the biocidal compounds decompose in the presence of alkali. Exemplary of alkali-sensitive compounds are 5-chloro-2-methyl-4-isothiazolin-3-one and 2-methyl-4-isothiazolin-3-one. Accordingly, the pH of the compositions of the present invention which are alkali sensitive should be maintained at a value no greater than about 8.

IX. Personal Care

The pH responsive polymer of the present invention is suitable in the preparation of personal care (cosmetics, toiletries, health and beauty aids, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; anti-acne products; anti-aging products (exfoliant, keratolytic, anticellulite, antiwrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to basic composition to which an effective amount of the hydrophobic polymer can be incorporated for achieving a beneficial or desirable, physical or chemical, effect therein during storage and/or usage.

In one embodiment, the present invention is directed to a personal care composition comprising water, one or more surfactants, and a pH responsive polymer according to the present invention.

In one embodiment, the personal care composition comprises, based on 100 parts by weight ("pbw") of the personal care composition, from about 10 to about 80 pbw, more typically from about 20 to about 70 pbw, water, from about 1 to about 50 pbw of one or more surfactants and from about 0.05 to about 20 pbw of the pH responsive polymer of the present invention.

Suitable surfactants include anionic surfactants, cationic surfactants, non-ionic surfactants, zwitterionic surfactants, and mixtures thereof.

Suitable anionic surfactants are known compounds and include, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, isethionates, and taurates, as well as mixtures thereof, such as for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium monoalkyl phosphate, sodium dialkyl phosphate, sodium lauryl sarcosinate, lauroyl sarcosine, cocoyl sarcosinate, ammonium cocyl sulfate, sodium cocyl sulfate, potassium cocyl sulfate, monoethanolamine cocyl sulfate, sodium tridecyl benzene sulfonate, sodium dodecyl benzene sulfonate, and mixtures thereof.

The cationic counterion of the anionic surfactant is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations may be used.

Suitable cationic surfactants are known compounds and include, for example, mono-cationic surfactants according to structure (XX) below:

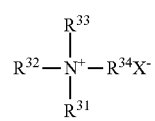

XX wherein:

R31, R32, R33 and R34 are independently hydrogen or an organic group, provided that at least one of R31, R32, R33 and R34 is not hydrogen, and [0108] X⁻ is an anion, as well as mixtures of such compounds If one to three of the R31, R32, R33 and R34 groups are each hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine.

For quaternary ammonium compounds (generally referred to as quats) R31, R32, R33 and R34 may be the same or different organic group, but may not be hydrogen. In one embodiment, R31, R32, R33 and R34 are each C8-C24 branched or linear hydrocarbon groups which may comprise additional functionality such as, for example, fatty acids or derivatives thereof, including esters of fatty acids and fatty acids with alkoxylated groups; alkyl amido groups; aromatic rings; heterocyclic rings; phosphate groups; epoxy groups; and hydroxyl groups. The nitrogen atom may also be part of a heterocyclic or aromatic ring system, e.g., cetethyl morpholinium ethosulfate or steapyrium chloride.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), babassuamidopropalkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride; branched and/or unsaturated cationic surfactants such as isostearylaminopropalkonium chloride or olealkonium chloride; long chain cationic surfactants such as stearalkonium chloride and behentrimonium chloride; as well as mixtures thereof.

Suitable anionic counterions for the cationic surfactant include, for example, chloride, bromide, methosulfate, ethosulfate, lactate, saccharinate, acetate and phosphate anions.

Suitable nonionic surfactants are known compounds and include amine oxides, fatty alcohols, alkoxylated alcohols, fatty acids, fatty acid esters, and alkanolamides. Suitable amine oxides comprise, (C10-C24) saturated or unsaturated branched or straight chain alkyl dimethyl oxides or alkyl amidopropyl amine oxides, such as for example, lauramine oxide, cocamine oxide, stearamine oxide, stearamidopropylamine oxide, palmitamidopropylamine oxide, decylamine oxide as well as mixtures thereof. Suitable fatty alcohols include, for example, (C10-C24) saturated or unsaturated branched or straight chain alcohols, more typically (C10-C20) saturated or unsaturated branched or straight chain alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof. Suitable alkoxylated alcohols include alkoxylated, typically ethoxylated, derivatives of (C10-C24) saturated or unsaturated branched or straight chain alcohols, more typically (C10-C20) saturated or unsaturated branched or straight chain alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoxylated alcohols may be used. Suitable fatty acids include (C10-C24) saturated or unsaturated carboxylic acids, more typically (C10-C22) saturated or unsaturated carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof. Suitable fatty acid esters include esters of (C10-C24) saturated or unsaturated carboxylic acids, more typically (C10-C22) saturated or unsaturated carboxylic acids, for example, propylene glycol isostearate, propylene glycol oleate, glyceryl isostearate, and glyceryl oleate, and mixtures thereof. Suitable alkanolamides include aliphatic acid alkanolamides, such as cocamide MEA (coco monoethanolamide) and cocamide MIPA (coco monoisopropanolamide), as well as alkoxylated alkanolamides, and mixtures thereof.

Suitable amphoteric surfactants are known compounds and include for example, derivatives of aliphatic secondary and tertiary amines in which the aliphatic radical can be straight chain or branched and wherein one of the aliphatic substituents contains from about 8 to about 18 carbon atoms and one contains an anionic water-solubilizing group as well as mixtures thereof. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyliminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the amphoteric surfactant comprises sodium lauroampoacetate, sodium lauroampopropionate, disodium lauroampodiacetate, sodium cocoamphoacetate, disodium cocoamphodiacetate or a mixture thereof.

Suitable Zwitterionic surfactants are known compounds. Any Zwitterionic surfactant that is acceptable for use in the intended end use application and is chemically stable at the required formulation pH is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to about 24 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine and alkylamidopropylhydroxy sultaines.

In one embodiment, the personal care composition further comprises an electrolyte, typically in an amount of up to about 20 pbw per 100 pbw of the personal care composition. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulfonates or naphthalene sulfonate formaldehyde copolymers.

In one embodiment, the personal care composition comprises water, an anionic surfactant, a structuring agent for the anionic surfactant, and a pH responsive polymer according to the present invention and exhibits one or more lamellar surfactant phases. "Lamellar surfactant phases" are phases which comprise one or more surfactant bilayers, typically a plurality of surfactant bilayers separated by liquid medium. Lamellar phases include spherulite phases and the typical form of the liquid crystal G-phase, as well as mixtures thereof. "G-phases", which are sometimes referred to in the literature as "L, phases", are typically pourable, non-Newtonian, anisotropic products that are cloudy looking and exhibit a characteristic "smeary" appearance on flowing. Lamellar phases can exist in several different forms, including domains of parallel sheets, which constitute the bulk of the typical G-phases described above and spherulites formed from a number of concentric spherical shells, each of which is a bilayer of surfactant. In this specification the term "G-phase" will be reserved for compositions, which are at least partly of the former type. The spherulites are typically between 0.1 and 50 microns in diameter and so differ fundamentally from micelles. The surfactant phase morphology of the structured surfactant composition is observed, for example, using an optical microscope under cross-polarized light at about 40× magnification.

In one embodiment, the personal care composition of the present invention exhibits structured surfactant properties, that is, shear-thinning viscosity and a capacity to suspend water insoluble or partially water soluble components.

As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains undissolved in the aqueous composition.

As used herein, characterization of an aqueous composition as "capable of suspending", or as being "able of suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

In one embodiment, the personal care composition of the present invention comprises, based on 100 pbw of the composition from about 5 to about 40 parts pbw, more typically from about 10 to about 30 pbw, and still more typically from about 15 to about 25 pbw, of the anionic surfactant and from about 0.1 to about 25 pbw, more typically, from about 0.5 to about 10 pbw, of a structuring agent.

In one embodiment, the pH of the lamellar phase containing personal care composition is from about 5.0 to about 7.0, more typically from about 5.5 to about 6.5.

Suitable anionic surfactants include those described above. In one embodiment of the lamellar phase containing personal care composition, the anionic surfactant comprises one or more branched and/or unsaturated anionic surfactants. Suitable branched anionic surfactants include, for example, sodium trideceth sulfate, sodium tridecyl sulfate, ammonium trideceth sulfate, and ammonium tridecyl sulfate.

Suitable structuring agents include cationic surfactants, amphoteric surfactants, fatty alcohols, alkoxylated alcohols, fatty acids, fatty acid esters, alkanolamides, amine oxides, and electrolytes, and mixtures thereof. An effective amount of such structuring agent is one that promotes and/or does not interfere with the formation of a lamellar surfactant phase. Suitable cationic surfactants, amphoteric surfactants, fatty alcohols, alkoxylated alcohols, fatty acids, fatty acid esters, alkanolamides, amine oxides, and electrolytes are described above.

Typically, the greater the amount of surfactant present in relation to its solubility, the smaller the amount electrolyte that may be required in order to form a structure capable of supporting solid materials and/or to cause flocculation of the structured surfactant. In one embodiment, the composition contains a sufficient amount of an electrolyte to promote formation lamellar surfactant phases.

In one embodiment, the personal care composition of the present invention further comprises, typically in an amount of from greater than 0 pbw to about 50 pbw, more typically form about 1 to about 30 pbw, per 100 pbw of the personal care composition, one or more "benefit agents" that is, materials that provide a personal care benefit, such as moisturizing or conditioning, to the user of the personal care composition, such as, for example, emollients, moisturizers, conditioners, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the personal care composition is a hair styling composition. Suitable hair styling compositions may be in the form of a gel, mousse, or spray and may be applied to the hair and/or skin, for example, by hand or by spraying, as appropriate in view of the form of the composition.

In one embodiment, the personal care composition is a hair styling gel that comprises a hair styling polymer, a pH responsive polymer of the present invention, and a carrier, such as water, a (C2-C6)alkanol, or a mixture thereof.

Suitable hair styling polymers typically comprise multiple cationic sites per molecule and include, for example, polyquaternium-11, polyquaternium4, polyquaternium-7, polyquaternium-16, polyquaternium-28, polyquaternium-44, polyquaternium-46, polyquaternium-55, polyquaternium-68 and polyquaternium-88. Suitable hair styling polymers also include, but are not limited to copolymers of polyvinylpyrrolidone, vinyl acetate, polyvinylcaprolactam, methylether maleic acid, acrylamides, octylacrylamide, butylaminoethyl, crotonic acid, dimethylaminopropyl methacrylate and dimethylaminoethyl methacrylate, and mixtures thereof.

As used herein, the term "mousse" means a composition that is in the form of a foam when applied. In one embodiment, the personal care composition is a hair styling mousse is packaged in a pressurized container and comprises a hair styling polymer, a pH responsive polymer of the present invention, a carrier, such as water, a (C2-C6)alkanol, a propellant suitable for foaming the composition when the composition is dispensed from the container. Suitable propellants are liquefiable gases, such as, for example, propane, butane, isobutane, nitrogen, carbon dioxide, nitrous oxide, 1,2-difluoroethane.

In one embodiment, the personal care composition is a hair spray composition suitable for spray application from a container that is equipped with a mechanical sprayer, comprising a hair styling polymer, a pH responsive polymer of the present invention, and a carrier, such as water, a (C2-C6)alkanol, or a mixture thereof.

In one embodiment, the personal care composition is an aerosol hair spray composition suitable for spray application from a pressurized container and comprises, a hair styling polymer, a carrier, typically a (C1-C6)alkanol or a (C7-C10) isoparaffin, a pH responsive polymer of the present invention, and a propellant suitable for aerosol delivery of the hair spray composition to the hair. Suitable propellants are those described above in regard to the hair styling mousse embodiment of the personal care composition of the present invention.

The hair styling gel, mousse, and hair spray may in each case, optionally further comprise one or more emollients, conditioning agents, shine enhancers, moisture and heat sensitive moieties, or a mixture thereof. Suitable emollients include, for example, PEG-40 castor oil, glycerol, propylene glycol, butylene glycol. Suitable conditioning and shine agents include, for example, quaternized and/or hydrolyzed proteins of honey, soy, wheat, guar or maize, cetyl alcohol, stearyl alcohol, ceteareth-20, isopropyl palmitate, cyclopentasiloxane, cyclomethicone, trimethylsilyamodimethicone, phenyltrimethicone, ethoxylated/propylated dimethicone, dimethiconol, panthenol, tocopherol acetate, tocopherol, cetrimmonium chloride, hair keratin and silk amino acids and ethoxylated/propoxylated waxes of fruit and vegetable origin.

The personal care composition according to the present invention may optionally further comprise one or more adjuvants, such as, for example, preservatives such as benzyl alcohol, methyl paraben, propyl paraben and imidazolidinyl urea; pH adjusting agents such as citric acid, succinic acid, phosphoric acid, sodium hydroxide, sodium carbonate; dyes, and sequestering agents such as disodium ethylenediamine tetra-acetate.

In general, personal care compositions may optionally comprise, based on 100 pbw of the personal care composition and independently for each such adjuvant, from about 0 to about 10 pbw, typically from 0.5 pbw to about 5.0 pbw, of such optional adjuvants, depending on the desired properties of the personal care composition.

The pH responsive polymer of the present application is useful as a component in aqueous fluid compositions used in oilfield applications.

In one embodiment, an aqueous fluid composition of the present invention comprises water and a pH responsive polymer of the present invention, typically from about 0.05 to about 40 pbw, more typically 0.1 pbw to 20 pbw, even more typically form about 1 to about 10 pbw of the pH responsive polymer per 100 pbw composition, wherein the pH of the composition is greater than or equal to about 6, more typically, from about 6 to about 10.

X. Use with Materials in Geological Formations

A. Fracturing Fluids

In one embodiment, the aqueous fluid composition of the present invention is used as the fracturing fluid in a method for hydraulic fracturing of a geologic formation to stimulate the production of fluids, such as oil and/or natural gas, from the formation. The fracturing fluid is injected through a wellbore and against a surface of the formation at a pressure and flow rate at least sufficient to initiate and/or extend one or more fractures in the formation. Typically, the fracturing fluid further comprises a proppant dispersed in the fracturing fluid. Suitable proppants are inorganic particles, such as sand, bauxite particles, or glass beads and are typically in the range of from about 20 to about 40 mesh. Such fracturing fluid compositions typically contain, based on 100 pbw of the liquid component of such composition, from about 90 pbw to about 100 pbw water, from about 0.1 pbw to about 10 pbw pH responsive polymer, and from about 10 pbw to about 150 pbw proppant. The proppant particles are transported into fractures in the geologic formation by the pressurized fracturing fluid stream and keep the fractures from closing back down when the stream of fracturing fluid is discontinued. The proppant-filled fractures provide permeable channels through which the formation fluids can flow to the wellbore and then be withdrawn. Hydraulic fracturing fluids are subject to high temperatures and shear rates.

The polymer and composition of the present invention may be used in the fracturing fluid in an amount of from 0.01 to 5% by weight of the fluid.

A.1. Crosslinking Agent

A crosslinking agent may be used with the fracturing fluids. The crosslinking agents used may include aluminum or antimony or Group 4 transition metal compound crosslinking agents. The crosslinking agent may include zirconium, titanium and hafnium crosslinking agents, and combinations of these, and may include organo-metallic compounds. Examples of suitable zirconium crosslinking agents include zirconium triethanolamine, L-glutamic acid-triethanolamine-zirconium, zirconium diethanolamine, zirconium tripropanolamine, and zirconium lactate complexes, and/or the related salts, and/or their mixtures. Examples of titanium crosslinking agents include titanium triethanolamine, dihydroxybis(ammonium lactato)titanium, and titanium acetylacetonate. The crosslinking agent may be included in the fluid in an amount of from about 0.01% to about 1.5% by weight of the fluid, more particularly, from about 0.02% to about 0.3% by weight of the fluid.

A.2. Buffering Agent

A hydroxyl ion releasing agent or buffering agent may be employed to adjust the pH or buffer the fluid, i.e., moderate amounts of either a strong base or acid may be added without causing any large change in pH value of the fluid. These may useful in changing the rate of crosslinking. Alkaline amine or polyamine compounds useful to raise the pH to the desirable level are outlined in U.S. Pat. No. 4,579,670, and include tetramethylenediamine, triethylenetetramine, tetraethylenepentamine (TEPA), diethylenetriamine, triethylenediamine, triethylenepentamine, ethylenediamen and similar compounds. The alkali metal hydroxides, e.g., sodium hydroxide, and carbonates can also be used. Other acceptable materials are $Ca(OH)_2$, $Mg(OH)_2$, $Bi(OH)_3$, $Co(OH)_2$, $Pb(OH)_2$, $Ni(OH)_2$, $Ba(OH)_2$, and $Sr(OH)_2$. Acids such as hydrochloric acid, sulfuric acid, nitric acid, citric acid, acetic acid, fumaric acid, maleic acid, can be used to lower the pH.

In various embodiments, the buffering agent is a combination of a weak acid and a salt of the weak acid; an acid salt with a normal salt; or two acid salts. Examples of suitable buffering agents are acetic acid-Na acetate; $NaH_2PO_4$—$Na_2PO_4$; sodium carbonate-sodium bicarbonate; and sodium bicarbonate, or other like agents. By employing a buffering agent instead of merely a hydroxyl ion producing material, a fluid is provided which is more stable to a wide range of pH values found in local water supplies and to the influence of acidic materials located in formations and the like.

A.3. Gas Component

The fracturing fluids may contain a gas component, as discussed above. The gas component may be provided from any suitable gas that forms an energized fluid or foam when introduced into the aqueous medium. See, for example, U.S. Pat. No. 3,937,283 (Blauer et al.), hereinafter incorporated by reference. The gas component may comprise a gas selected from nitrogen, air, argon, carbon dioxide, and any mixtures thereof. Particularly useful are the gas components of nitrogen or carbon dioxide, in any quality readily available. The gas component may assist in the fracturing, and also the capacity of the fluid to carry solids, such as proppants. The presence of the gas also enhances the flowback of the fluid to facilitate cleanup. The fluid may contain from about 10% to about 90% volume gas component based upon total fluid volume percent, more particularly from about 20% to about 80% volume gas component based upon total fluid volume percent, and more particularly from about 30% to about 70% volume gas component based upon total fluid volume percent.

A.4. Breaker

Fracturing fluids based on the invention may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. The breakers may include persulfates such as ammonium persulfate, sodium persulfate, and potassium persulfate, bromates such as sodium bromate and potassium bromate, periodates, metal peroxides such as calcium peroxide, chlorites, and the like, and the combinations of these breakers, live or encapsulated.

A.5. Proppant

Embodiments of the invention used as fracturing fluids may also include proppant particles substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it will typically be from about 20 mesh (0.841 mm) to about 100 mesh (0.0059 mm) in size. With synthetic proppants, mesh sizes of about 8 (0.937 mm) or greater may be used. Naturally occurring materials may be underived and/or unprocessed naturally occurring materials, as well as materials based on naturally occurring materials that have been processed and/or derived. Suitable examples of naturally occurring particulate materials for use as proppants include, but are not necessarily limited to: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particalization, processing, etc. Further information on nuts and composition thereof may be found in Encyclopedia of Chemical Technology, Edited by Raymond E. Kirk and Donald F. Othmer, Third Edition, John Wiley & Sons, Volume 16, pages 248-273 (entitled "Nuts"), Copyright 1981, which is incorporated herein by reference.

The concentration of proppant in the fluid can be any concentration known in the art, and will preferably be in the range of from about 0.03 to about 3 kilograms of proppant added per liter of liquid phase. Also, any of the proppant particles can further be coated with a resin to potentially improve the strength, clustering ability, and flow back properties of the proppant.

A.6. Aqueous Media

The aqueous medium of the fracturing fluids of the present invention may be water or brine. In those embodiments of the invention where the aqueous medium is a brine, the brine is water comprising an inorganic salt or organic salt. Inorganic salts may include alkali metal halides, such as potassium chloride. The carrier brine phase may also comprise an organic salt, such as sodium or potassium formate. Inorganic divalent salts include calcium halides, such as calcium chloride or calcium bromide. Sodium bromide, potassium bromide, or cesium bromide may also be used. The salt may be chosen for compatibility reasons i.e. where the reservoir drilling fluid used a particular brine phase and the completion/clean up fluid brine phase is chosen to have the same brine phase. Typical salt levels are 2 to 30 wt% salt based on overall composition of the aqueous brine. The most common level of salt in brine is 2-10 weight% sodium chloride, potassium chloride or mixtures thereof based on overall composition of the aqueous brine.

A.7. Fiber Component

A fiber component may be included in the fracturing fluids of the invention to achieve a variety of properties including improving particle suspension, and particle transport capabilities, and gas phase stability. Fibers used may be hydrophilic or hydrophobic in nature, but hydrophilic fibers may be useful for some applications. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON polyethylene terephthalate (PET) fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be include at concentrations from about 1 to about 15 grams per liter of the liquid phase of the fluid, in certain applications the concentration of fibers may be from about 2 to about 12 grams per liter of liquid, and in others from about 2 to about 10 grams per liter of liquid.

A.8. Other Optional Ingredients

Fluid embodiments of fracturing fluids of the invention may further contain other additives and chemicals known to be commonly used in oilfield applications by those skilled in the art. These include, but are not necessarily limited to, materials such as surfactants in addition to those mentioned herein, clay stabilizers such as tetramethyl ammonium chloride and/or potassium chloride, breaker aids in addition to those mentioned herein, oxygen scavengers, alcohols, scale inhibitors, corrosion inhibitors, fluid-loss additives, bactericides, and the like. Also, they may include a co-surfactant to optimize viscosity or to minimize the formation of stable emulsions that contain components of crude oil or a polysaccharide or chemically modified polysaccharide, polymers such as cellulose, derivatized cellulose, guar gum, derivatized guar gum, xanthan gum, or synthetic polymers such as polyacrylamides and polyacrylamide copolymers, oxidizers such as ammonium persulfate and sodium bromate, and biocides such as 2,2-dibromo-3-nitrilopropionamine. The fluid should be substantially devoid of hectorite clay or other clay components and such components may be present in the fluid only in amounts of less than 0.1% by weight.

Aqueous fluid embodiments of the invention may also comprise an organoamino compound. Examples of suitable organoamino compounds include, but are not necessarily limited to, tetraethylenepentamine (TEPA), triethylenetetramine, pentaethylenehexamine, triethanolamine, and the like, or any mixtures thereof. When organoamino compounds are used in fluids of the invention, they are incorporated at an amount from about 0.01 wt % to about 2.0 wt % based on total liquid phase weight. The organoamino compound may be incorporated in an amount from about 0.05 wt % to about 1.0 wt % based on total weight of the fluid. A particularly useful organoamino compound is tetraethylenepentamine (TEPA).

A.9. Hydraulic Fracturing Techniques

The fluids of the invention may be used for hydraulically fracturing a subterranean formation. Techniques for hydraulically fracturing a subterranean formation are known to persons of ordinary skill in the art, and involve pumping the fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications", Encyclopedia of Polymer Science and Engineering, vol. 10, pp. 328-366 (John Wiley & Sons, Inc. New York, N.Y., 1987) and references cited therein, the disclosures of which are incorporated herein by reference thereto.

In the fracturing treatment, fluids of the present invention may be used in the pad treatment, the proppant stages, or both. The components of the liquid phase may be mixed on the surface. Alternatively, the fluid may be prepared on the surface and pumped down tubing while any gas component could be pumped down the annulus to mix down hole, or vice versa.

In hydraulic fracturing the fracturing fluid comprising water soluble polymer and at least one nonionic surfactant is pumped into the targeted formation at a rate in excess of what can be dissipated through the natural permeability of the formation rock. The fracturing fluids result in a pressure build up until such pressure exceeds the strength of the formation rock. When this occurs, the formation rock fails and a so-called "fracture" is initiated. With continued pumping, the fracture grows in length, width and height.

At a predetermined time in the pumping process, solid particulate is typically added to the fluid that is being pumped. This particulate is carried down the well, out of the wellbore and deposited in the created fracture. It is the purpose of this specially designed particulate to keep the fracture from "healing" to its initial position (after pumping has ceased). The particulate is said to be propping open the fracture and is therefore designated as "proppant". The fracture, which is generated by the application of this stimulation technique, creates a conductive path to the wellbore for the hydrocarbon.

Typical proppant is selected from the group consisting of gravel, quartz sand grains, sintered bauxite, glass and ceramic beads, walnut shell fragments, or aluminum pellets. The fracturing fluid may also include a thermal stabilizer, for example sodium thiosulfate, methanol, ethylene glycol, isopropanol, thiourea, and/or sodium thiosulfite. The fracturing fluid may also include KCl as a clay stabilizer.

B. Acidizing

Producing oil and gas wells have long been treated to stimulate production thereof utilizing a method termed "acidizing" in which an emulsion of an aqueous mineral acid either alone or in combination with various surfactants, corrosion inhibiting agents, and hydrocarbon oils is added to a producer well. Presumably, such treatments tend to remove deposits from the area of the subterranean oil or gas formation immediately adjacent to the production well bore, thus increasing the permeability of the formation and allowing residual oil or gas to be recovered through the well bore. Another object of such "acidizing" treatment of oil or gas producer wells is the removal of water from the interstices of the formation by the use of a composition which materially lowers the interfacial forces between the water and the oil or gas. Various surface-active agents have been recommended for this use.

Producing oil and gas wells have long been treated to stimulate production thereof utilizing a method termed "acidizing" in which an emulsion of an aqueous mineral acid either alone or in combination with various surfactants, corrosion inhibiting agents, and hydrocarbon oils is added to a producer well. Presumably, such treatments tend to remove deposits from the area of the subterranean oil or gas formation immediately adjacent to the production well bore, thus increasing the permeability of the formation and allowing residual oil or gas to be recovered through the well bore. Another object of such "acidizing" treatment of oil or gas producer wells is the removal of water from the interstices of the formation by the use of a composition which materially lowers the interfacial forces between the water and the oil or gas. Various surface-active agents have been recommended for this use.

Acidizing, and fracturing procedures using acidic treatment fluids, are commonly carried out in subterranean well formations to accomplish a number of purposes including, but not limited to, to facilitate the recovery of desirable hydrocarbons from the formation. As used herein, the term "treatment fluid" refers to any fluid that may be used in a subterranean application in conjunction with a desired function and/or for a desired purpose. The term "treatment fluid" does not imply any particular action by the fluid or any component thereof.

One commonly used aqueous acidic treatment fluid comprises hydrochloric acid. Other commonly used acids for acidic treatment fluids include hydrofluoric acid, acetic acid, formic acid, citric acid, ethylene diamine tetra acetic acid ("EDTA"), glycolic acid, sulfamic acid, and derivatives or combinations thereof.

Acidic treatment fluids are used in various subterranean operations. For example, formation acidizing or "acidizing" is a method for, among other purposes, increasing the flow of desirable hydrocarbons from a subterranean formation. In a matrix acidizing procedure, an aqueous acidic treatment fluid is introduced into a subterranean formation via a well bore therein under pressure so that the acidic treatment fluid flows into the pore spaces of the formation and reacts with (e.g., dissolves) the acid-soluble materials therein. As a result, the pore spaces of that portion of the formation are enlarged, and the permeability of the formation may increase. The flow of hydrocarbons from the formation therefore may be increased because of the increase in formation conductivity caused, inter alia, by dissolution of the formation material. In fracture acidizing procedures, one or more fractures are produced in the formation(s) and an acidic treatment fluid is introduced into the fracture(s) to etch flow channels therein. Acidic treatment fluids also may be used to clean out well bores to facilitate the flow of desirable hydrocarbons. Other acidic treatment fluids may be used in diversion processes and well bore clean-out processes. A specific example is filter cake removal.

To increase the viscosity of an aqueous acidic treatment fluid, a suitable gelling agent may be included in the treatment fluid (often referred to as "gelling" the fluid). Gelling an aqueous acidic treatment fluid may be useful, among other purposes, to prevent the acid from becoming prematurely spent and inactive. Additionally, gelling an aqueous acidic treatment fluid may enable the development of wider fractures so that the gelled acidic treatment fluid may delay the interaction of the acid with an acid soluble component in the well bore or the formation. Moreover, gelling an aqueous acidic treatment fluid may permit better fluid loss control.

Acidic treatment fluids used in subterranean operations are predominantly water-based fluids that comprise gelling agents to increase their viscosities. Common gelling agents include polysaccharides (such as xanthan), synthetic polymers (such as polyacrylamide), and surfactant gel systems. To assist the gelling agents in maintaining these viscosities in the presence of the high temperatures and slat concentrations experienced downhole the composition includes the polymer combinations of the present invention.

The aqueous base fluids of the acidic treatment fluids of the present invention generally comprise fresh water, salt water, sea water, a brine (e.g., a saturated salt water or formation brine), or a combination thereof. Other water sources may be used, including those comprising monovalent, divalent, or trivalent cations (e.g., magnesium, calcium, zinc, or iron) and, where used, may be of any weight. If a water source is used that contains such divalent or trivalent cations in concentrations sufficiently high to be problematic, then such divalent or trivalent salts may be removed, either by a process such as reverse osmosis, or by raising the pH of the water in order to precipitate out such divalent salts to lower the concentration of such salts in the water before the water is used. Another method would be to include a chelating agent to chemically bind the problematic ions to prevent their undesirable interactions with the clarified xanthan. Suitable chelants include, but are not limited to, citric acid or sodium citrate, ethylene diamine tetra acetic acid ("EDTA"), hydroxyethyl ethylenediamine triacetic acid ("HEDTA"), dicarboxymethyl glutamic acid tetrasodium salt ("GLDA"), diethylenetriaminepentaacetic acid ("DTPA"), propylenediaminetetraacetic acid ("PDTA"), ethylenediaminedi(o-hydroxyphenylacetic) acid ("EDDHA"), glucoheptonic acid, gluconic acid, and the like, and nitrilotriacetic acid ("NTA"). Other chelating agents also may be suitable. One skilled in the art will readily recognize that an aqueous base fluid containing a high level of multi-valent ions should be tested for compatibility prior to use.

The gelling agents comprising the polymers of the present invention may be present in an acidic treatment fluid of the present invention in an amount of from about 1 lb/Mgal to about 200 lb/Mgal. In embodiments wherein the gelling agents comprising clarified xanthan further comprise scleroglucan, one may include about 1 lb/Mgal to about 200 lb/Mgal of scleroglucan. In an acidic treatment fluid that comprises hydrochloric acid, one may include about 1 to about 200 lb/Mgal of scleroglucan. In embodiments wherein the gelling agents comprising clarified xanthan further comprise diutan, one may include about 1 to about 200 lb/Mgal of diutan. In an acidic treatment fluid that comprises about 15% hydrochloric acid, one may include about 1 to about 200 lb/Mgal of diutan. In some embodiments, one may include about 10 to about 150 lb/Mgal of clarified xanthan, scleroglucan, and/or diutan. A person of skill in the art with the benefit of this disclosure will recognize that any specific concentration or narrower range of concentrations of the gelling agents of the present invention encompassed by the broader concentration ranges specifically articulated above may be used and/or may be particularly advantageous for a particular embodiment of the present invention.

In certain embodiments, the acidic treatment fluids of the present invention also may comprise any additional additive that may be suitable in a particular application of the present invention, including, but not limited to, any of the following: hydrate inhibitors, clay stabilizers, bactericides, salt substitutes (such as tetramethyl ammonium chloride), relative permeability modifiers (such as HPT-1™. chemical additive available from Halliburton Energy Services, Duncan, Okla.), sulfide scavengers, fibers, nanoparticles, consolidating agents (such as resins and/or tackifiers), corrosion inhibitors, corrosion inhibitor intensifiers, pH control additives, surfactants, breakers, fluid loss control additives, scale inhibitors, asphaltene inhibitors, paraffin inhibitors, salts, bactericides, crosslinkers, stabilizers, chelants, foamers, defoamers, emulsifiers, demulsifiers, iron control agents, solvents, mutual solvents, particulate diverters, gas phase, carbon dioxide, nitrogen, other biopolymers, synthetic polymers, friction reducers, combinations thereof, or the like. The acidic treatment fluids of the present invention also may include other additives that may be suitable for a given application, as will be recognized by a person of ordinary skill in the art, with the benefit of this disclosure.

While typically not required, the acidic treatment fluids of the present invention also may comprise breakers capable of reducing the viscosity of the acidic treatment fluid at a desired time. Examples of such breakers that may be suitable for the acidic treatment fluids of the present invention include, but are not limited to, sodium chlorite, hypochlorites, perborates, persulfates, peroxides (including organic peroxides), enzymes, derivatives thereof, and combinations thereof. Other suitable breakers may include suitable acids. Examples of peroxides that may be suitable include tert-butyl hydroperoxide and tert-amyl hydroperoxide. A breaker may be included in an acidic treatment fluid of the present invention in an amount and form sufficient to achieve the desired viscosity reduction at a desired time. The breaker may be formulated to provide a delayed break, if desired. For example, a suitable breaker may be encapsulated if desired. Suitable encapsulation methods are known to those skilled in the art. One suitable encapsulation method that may be used involves coating the breaker(s) with a material that will degrade when placed downhole so as to release the breaker at the appropriate time. Coating materials that may be suitable include, but are not limited to, polymeric materials that will degrade when downhole. The terms "degrade," "degradation," or "degradable" refer to both the two relatively extreme cases of hydrolytic degradation that the degradable material may undergo, i.e., heterogeneous (or bulk erosion) and homogeneous (or surface erosion), and any stage of degradation in between these two. This degradation can be a result of, inter alia, a chemical or thermal reaction or a reaction induced by radiation. Suitable examples of materials that can undergo such degradation include polysaccharides such as dextran or cellulose; chitins; chitosans; proteins; aliphatic polyesters; poly (lactides); poly(glycolides); poly(.epsilon.-caprolactones); poly(hydroxybutyrates); poly(anhydrides); aliphatic polycarbonates; orthoesters, poly(orthoesters); poly(amino acids); poly(ethylene oxides); polyphosphazenes; derivatives thereof; and combinations thereof. If used, a breaker should be included in a composition of the present invention in an amount sufficient to facilitate the desired reduction in viscosity in a viscosified treatment fluid. For instance, peroxide concentrations that may be used vary from about 0.1 to about 10 gallons of peroxide per 1000 gallons of the acidic treatment fluid.

C. Enhanced Oil Recovery

The present invention may be employed with other techniques to further improve hydrocarbon recovery from subterranean formations. Initially, oil is produced from the fractured formation by pressure depletion (primary recovery). In this method, the differential pressure between the formation and a production well or wells forces the oil contained within the formation toward a production well where it can be recovered. Traditionally secondary recovery processes through injection of water or gas are used to displace additional oil toward producing wells. Typically, up to about 35 percent of the oil which is initially contained in a formation can be recovered in average through primary and secondary recovery. This leaves a large quantity of oil within the formation. Additionally, some formations contain oil which is too viscous to be efficiently recovered from the formation using primary and secondary processes. Because of the need to recover a larger percentage of the oil from a formation, methods have been developed to recover oil which could not be recovered using only pressure depletion techniques. These methods are typically referred to as "enhanced oil recovery techniques" (EOR).

Thus, the present invention is also directed to a method for recovering crude oil from a subterranean formation, comprising introducing to the formation an aqueous medium comprising water or brine and the composition of the present invention including a combination of anionic polymer and cationic polymer described above.

The global average recovery factor for conventional oil fields is about 35% and it could be raised up to 50% through enhanced oil recovery. There are two essentials components to EOR: improving displacement efficiency and improving macroscopic sweep efficiency. The present invention enhances oil recovery by maintaining stable viscosity at high temperatures. The method of the invention is particularly useful in the stimulation of oil and gas wells which have failed to respond to acidizing treatment of the producing well including the use of various acids with various surfactants.

C.1. Chemical Flooding

A promising EOR method is an enhanced oil recovery process referred to as chemical flooding which generally covers the use of polymer and/or surfactant slugs. In polymer flooding, a polymer solution is injected to displace oil toward producing wells. The polymer solution is designed to develop a favorable mobility ratio between the injected polymer solution and the oil/water bank being displaced ahead of the polymer. However, the use of polymer is not always satisfactory as many polymer solutions are sensitive to brine type and concentration which can affect the apparent viscosity of the solution. In surfactant flooding, an aqueous solution containing surfactant is injected into the oil rich formation. Residual oil drops are deformed as a result of low Interfacial Tension provided by surfactant solution and drops are displaced through the pore throats and displaced oil is the recovered. See U.S. Pat. No. 7,789,160 to Hough et al. incorporated herein by reference in its entirety.

The present compositions advantageously are compatible with anionic surfactants typically used to decrease interfacial tension to also assist in enhancing oil recovery from subterranean formations.

The present invention proves enhanced oil recovery. For example, the present invention is also directed to a method for recovering crude oil from a subterranean formation, comprising introducing to the formation an aqueous medium comprising water or brine and the composition of the present invention including a combination of polyanionic polymer and polycationic polymer described above.

There are two important components to EOR: improving displacement efficiency and improving macroscopic sweep efficiency. The present invention enhances oil recovery by maintaining stable viscosity at high temperatures. The method of the invention is particularly useful in the stimulation of oil and gas wells which have failed to respond to acidizing treatment of the producing well including the use of various acids with various surfactants.

The present compositions advantageously are compatible with anionic surfactants typically used to decrease interfacial tension to also assist in enhancing oil recovery from subterranean formations.

The aqueous medium of the composition may be soft water, brackish water or brine. Typically the aqueous medium in compositions used to treat subterranean formations comprises brine.

C.2. Other Ingredients

Compositions of the invention may contain components in addition to water, the first cationic or cationaizable polymer, the second anionic or anionizable polymer and optional surfactants. Such additional components are, for example, co-solvents, acids, bases, buffers, chelating agents for the control of multivalent cations, freezing point depressants, etc.

For example, a hydrocarbon recovery composition according to the present invention may be provided to the hydrocarbon containing formation alone or with other compounds for enhancing oil recovery. For example, these other compounds may be other nonionic additives (e.g., alcohols, ethoxylated alcohols and/or sugar based esters). Some embodiments have less than 0.3 weight percent of one or more anionic surfactants (e.g. sulfates, sulfonates, ethoxylated sulfates, and/or phosphates). In some embodiments the composition has less than 0.3 wt % each of anionic surfactant, amphoteric surfactant and zwitterionic surfactant. If desired, there may be an absence of anionic surfactant, an absence of amphoteric surfactant, and an absence of zwitterionic surfactant.

C.3. Alcohol

Alcohol can be used as mutual solvent to reduce water saturation. The interfacial tension between oil and ethanol is much lower than between oil and brine.

Capillary forces of retention for the alcohol are much reduced compared to those for brine.

It has been reported that isopropyl or butyl alcohol plus methyl alcohol could be used in miscible displacement to increase oil recovery of naphtha and mineral oil.

Others have investigated enhanced oil recovery by alcohol flooding. Their process design was strongly guided by the ternary phase of alcohol/oil/brine. They showed that oil recovery was highly dependent on the choice of alcohol/oil/brine combinations. Others have reported that injection of appropriate combinations of oil-soluble and water-soluble solvents such as alcohols and ketones could significantly enhance oil recovery.

In an embodiment, an aliphatic nonionic additive may be used in a hydrocarbon recovery composition. As used herein, the term "aliphatic" refers to a straight or branched chain of carbon and hydrogen atoms. In some embodiments, an aliphatic portion of an aliphatic nonionic additive may have an average carbon number from 10 to 24. In some embodiments, an aliphatic portion of an aliphatic nonionic additive may have an average carbon number from 12 to 18. In some embodiments, the aliphatic nonionic additive may include a branched aliphatic portion. A branched aliphatic portion of an aliphatic nonionic additive may have an average carbon number from 16 to 17. In some embodiments, a branched aliphatic group of an aliphatic nonionic additive may have less than about 0.5 percent aliphatic quaternary carbon atoms. In an embodiment, an average number of branches per aliphatic nonionic additive ranges from about 0.1 to about 2.5. In other embodiments, an average number of branches per aliphatic nonionic additive ranges from about 0.7 to about 2.5.

Methyl branches may represent between about 20 percent to about 99 percent of the total number of branches present in the branched nonionic additive. In some embodiments, methyl branches may represent greater than about 50 percent of the total number of branches in a branched nonionic additive. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

In an embodiment, an aliphatic nonionic additive may be a long chain aliphatic alcohol. The term "long chain," as used herein, refers to a carbon chain having an average carbon number from 10 to 30. A long chain aliphatic alcohol (e.g., a long chain primary alcohol) may be purchased commercially (e.g., NEODOL alcohols manufactured by Shell Chemical Co., Houston, Tex.). In certain embodiments, a long chain aliphatic alcohol may be prepared by a variety of generally known methods. A long chain aliphatic alcohol may have an average carbon number from 10 to 24. In some embodiments, a long chain aliphatic alcohol may have an average carbon number from 12 to 18. In other embodiments, a long chain aliphatic alcohol may have an average carbon number from 16 to 17.

In an embodiment, a portion of the long chain aliphatic alcohol may be branched. Branched long chain aliphatic alcohols may be prepared by hydroformylation of a branched olefin. Preparations of branched olefins are described in U.S. Pat. No. 5,510,306 to Murray, entitled "Process for Isomerizing Linear Olefins to Isoolefins;" U.S. Pat. No. 5,648,584 to Murray, entitled "Process For Isomerizing Linear Olefins to Isoolefins" and U.S. Pat. No. 5,648,585 to Murray, entitled "Process For Isomerizing Linear Olefins to Isoolefins," all of which are incorporated by reference herein. Preparations of branched long chain aliphatic alcohols are described in U.S. Pat. No. 5,849,960 to Singleton et al., entitled "Highly Branched Primary Alcohol Compositions, and Biodegradable Detergents Made Therefrom;" U.S. Pat. No. 6,150,222 to Singleton et al., entitled "Highly Branched Primary Alcohol Compositions, and Biodegradable Detergents Made Therefrom;" U.S. Pat. No. 6,222,077 to Singleton et al., entitled "Highly Branched Primary Alcohol Compositions, and Biodegradable Detergents Made Therefrom," all of which are incorporated by reference herein.

In some embodiments, branches of a branched aliphatic group of a long chain aliphatic alcohol may have less than about 0.5 percent aliphatic quaternary carbon atoms. In an embodiment, an average number of branches per long chain aliphatic alcohol ranges from about 0.1 to about 2.5. In other embodiments, an average number of branches per alcohol ranges from about 0.7 to about 2.5.

Methyl branches may represent between about 20 percent to about 99 percent of the total number of branches present in the branched long chain aliphatic alcohol. In some embodiments, methyl branches may represent greater than about 50 percent of the total number of branches in a branched long chain aliphatic alcohol. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

C.4. Aliphatic Anionic Surfactants

In an embodiment, an aliphatic anionic surfactant may be used in a hydrocarbon recovery composition. In certain embodiments, an aliphatic portion of an aliphatic anionic surfactant may have an average carbon number from 10 to 24. In some embodiments, an aliphatic portion of an aliphatic anionic surfactant may have an average carbon number from 12 to 18. In other embodiments, an aliphatic portion of an aliphatic anionic surfactant may have an average carbon number from 16 to 17. In some embodiments, the aliphatic anionic surfactant may include a branched aliphatic portion. In some embodiments, a branched aliphatic group of an aliphatic anionic surfactant may have less than about 0.5 percent aliphatic quaternary carbon atoms. In an embodiment, an average number of branches per aliphatic anionic surfactant ranges from about 0.1 to about 2.5. In other embodiments, an average number of branches per aliphatic anionic surfactant ranges from about 0.7 to about 2.5.

Methyl branches may represent between about 20 percent to about 99 percent of the total number of branches present in the branched anionic surfactant. In some embodiments, methyl branches may represent greater than about 50 percent of the total number of branches in a branched anionic surfactant. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

In an embodiment which further employs aliphatic anionic surfactant, a solution may be provided which contains an effective amount of an aliphatic anionic surfactant selected from the group of compounds having the general formula: $R_1O(C_3H_6O)_m(C_2H_4O)_nYX$ wherein $R_1$ is a linear or branched alkyl radical, an alkenyl radical, or an alkyl or alkenyl substituted benzene radical, the non-aromatic portion of the radical containing from 6 to 24 carbon atoms; m has an average value of from 1 to 10; n has an average value of from 1 to 10; Y is a hydrophilic group; and X is a cation, preferably monovalent, for example N, K, $NH_4^+$. Y is a suitable hydrophilic group or substituted hydrophilic group such as, for example, the sulfate, sulfonate, phosphonate, phosphate or carboxylate radical. Preferably, $R_1$ is a branched alkyl radical having at least two branching groups and Y is a sulfonate or phosphate group.

C.5. Other Optional Additives for Enhanced Oil Recovery

The aqueous fluid of the present invention may, optionally, further comprise clay stabilization or sand stabilization material. During oil recovery processes, sands and other materials may become entrained in the recovered oil. This may be mitigated by the addition of a clay stabilization or sand stabilization material. Suitable clay stabilization or sand stabilization materials include epoxy resins, polyfunctional cationic polymers, such as poly(N-acrylamidomethyltnmethyl ammonium chloride) or poly(vinylbenzyltrimethyl ammonium chloride).

Other optional ingredients that may be added to the aqueous fluid of the present invention include, but are not limited to polymers such as biopolysaccharides, cellulose ethers, acrylamide-derived polymers, corrosion inhibitors, oxygen scavengers, bactericides, and so forth, and any combination thereof.

The aqueous fluid of the present invention is introduced into the crude oil-bearing formation, typically by injecting the fluid into the formation.

In the case of a carbonate formation having hydrophobic surfaces, addition of the organophosphorous material to the aqueous flooding fluid modifies such surfaces to increase the surface energy of such surfaces and render such surfaces more readily wettable by water. The surface modified formation more readily imbibes the aqueous flooding fluid, thus increasing the amount of aqueous fluid imbibed by the formation and increasing the amount of crude oil displaced from the formation by the aqueous fluid.

The aqueous fluid may be used in secondary or tertiary oil recovery processes, although the use of such fluids in other applications is also not excluded.

C.6. Methods of Use for Enhanced Oil Recovery

The aqueous medium utilized to form the solution including the organophosphorous material of the invention can be soft water, brackish water, or a brine. The aqueous fluid of the present invention is introduced into the crude oil-bearing formation, typically by injecting the fluid into the formation.

Optionally, after injection of the aqueous fluid comprising the present phosphate esters of the present invention addition to crude oil having generally the viscosity of the oil-bearing formation of the oil well to be treated, various hydrocarbon solvents may be employed to displace the aqueous solution out into the reservoir. Such hydrocarbon solvents as the low molecular weight, generally liquid hydrocarbons boiling below the gasoline range, such as the lower alkanes including butane, propane, pentane, hexane and heptane, as well as natural gasoline, petroleum naphtha and kerosene or mixtures of these hydrocarbons, are useful. Both sweet and sour crude oil is useful as a hydrocarbon to displace the aqueous solution out into the subterranean reservoir of oil or gas.

Optionally, injection of a preflush fluid may be utilized prior to injection of the aqueous fluid of the present invention. The preflush may consist of a hydrocarbon fluid, a brine solution, or simply water.

Also, injection of the aqueous fluid comprising the present phosphate esters may optionally be followed by an injection of a surfactant, a mobility control fluid or a polymeric flush, which is typically a polymer-thickened aqueous solution, using, for example the polymers disclosed above, into the formation to further enhance oil recovery. The polymeric solution is utilized to drive or push the now oil bearing surfactant flood out of the reservoir, thereby "sweeping" crude oil out of the reservoir. Further, the polymeric solution has a very high viscosity which helps to prevent what is referred to in the industry as channeling or "fingering", thus improving sweep efficiency.

This polymeric flush or mobility control fluid may once again be followed by a water flush which may be brine or saline or softened water, or fresh water.

Oil is recovered at a production well to be spaced apart from the injection well as the drive fluid pushes the mobility buffer slug which sweeps the oil out of the pores in the formation and to the production well. Once the water/oil emulsion reaches the surface, it is put into holding tanks where it is subsequently demulsified, thereby allowing the oil to separate from the water through the natural forces of gravity.

For example, a hydrocarbon recovery composition including the phosphate esters of the present invention may be added to a portion of hydrocarbon containing formation that may have an average temperature of less than 80° C. To facilitate delivery of an amount of the hydrocarbon recovery composition to the hydrocarbon containing formation, the hydrocarbon composition may be combined with water or brine to produce an injectable fluid. Typically about 0.01 to about 5 wt % of the phosphate ester, based on the total weight of injectable fluid, may be injected into the hydrocarbon containing formation through an injection well. In certain embodiments, the concentration of the hydrocarbon recovery composition injected through the injection well may be about 0.05% to about 3 wt. %, based on the total weight of injectable fluid. In some embodiments, the concentration of the hydrocarbon recovery composition may be about 0.1% to about 1 wt. % based on the total weight of injectable fluid.

In some embodiments, a hydrocarbon recovery composition may be added to a portion of a hydrocarbon containing formation.

XI. Home Care or Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, fabric softener, surfactants, builders, binders, bleach and fragrances.

In an embodiment the home care or industrial cleaning composition for cleaning fabrics or hard surfaces comprising, the composition of the present invention and a surfactant and a home care or industrial cleaner benefit agent.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

Examples of the prevent invention are set forth below. Unless otherwise indicated, all parts, percentages, and proportions herein are by weight.

EXAMPLES

Preparation of mono-[2-(methacryloyloxy)ethyl]phthalate (also known as 2-(2-carboxybenzoyloxy)ethyl methacrylate, MAEP)

Example 1

Imidazole as Catalyst

To a 0.5 liter jacketed reactor equipped with mechanical stirrer, condenser and addition funnel was added 2-hydroxyethy methacrylate (100 g, 0.77 mol) and 4-methoxyphenol (MEHQ) (0.16 g). The mixture was stirred with the initiation of 8% Oxygen in Nitrogen sub-surface purge. The mixture was heated to a set point of 80° C. and phthalic anhydride (39 g, 0.26 mol) was added through an addition funnel. Imidazole (1.57 g, 0.023 mol) was added to the mixture, resulting in an immediate exotherm. Additional phthalic anhydride (78 g, 0.53 mol) was added through the addition funnel over a 10 min. period. The reaction mixture was heated at 76° C. for 5 hours, allowed to cool and the MAEP product was isolated as a clear colorless viscous liquid (210 g). $^1$H NMR (CDCl$_3$), 400 MHz, ppm; 7.89 (1H, d, J=6.2 Hz), 7.69 (1H, d, J=7.1 Hz), 7.62-7.55 (2H, m), 6.12 (1H, s), 5.55 (1H, s), 4.58-4.56 (2H, m) 4.46-4.44 (2H, m), 1.91 (3H, s). Only residual quantities of 2-hydroxyethyl methacrylate and phthalic anhydride were observed in this isolated product.

Example 2

2,6-di-tert-butyl-4-((dimethylamino)methyl)phenol as catalyst

To a 0.25 liter 4-neck round bottom flask equipped with mechanical stirrer, condenser and heating mantel was added 2-hydroxyethy methacrylate (20 g, 0.153 mol). Stirring was initiated along with 8% Oxygen in Nitrogen sub-surface purge.

2,6-di-tert-butyl-4-((dimethylamino)methyl)phenol (1.2 g, 4.6 mmol) was added and the mixture was heated to a set point of 80° C. Phthalic anhydride (23.6 g, 0.16 mol) was then added over a ten minute period. The reaction mixture was heated at 82° C. for an additional 5 hours, allowed to cool and the MAEP product was isolated as a clear viscous liquid (41.3 g). $^1$H NMR consistent with that of Example 1.

Example 3

2,4,6-tris((dimethylamino)methylphenol as catalyst

To a 0.25 liter 4-neck round bottom flask equipped with mechanical stirrer, condenser and heating mantel was added 2-hydroxyethy methacrylate (20 g, 0.153 mol). Stirring was initiated along with 8% Oxygen in Nitrogen sub-surface purge. 2,4,6-tris((dimethylamino)methylphenol (0.41 g, 1.5 mmol) was added and the mixture was heated to a set point of 82° C. Phthalic anhydride (23.6 g, 0.16 mol) was then added over a ten minute period. The reaction mixture was heated at 82° C. for an additional 5 hours, allowed to cool and the MAEP product was isolated as a clear viscous liquid (40.5 g). $^1$H NMR consistent with that of Example 1.

The following examples evaluate of mono-[2-(methacryloyloxy)ethyl]phthalate (also known as 2-(2-carboxybenzoyloxy)ethyl methacrylate, MAEP) and mono-[2-(Methacryloyloxy)ethyl hexahydro]phthalate (MAHP)

Example 4

Preparation of HASE Systems

The typical polymerization ingredients and amounts used to make experimental HASE polymers for evaluation are summarized in TABLE 1.

TABLE 1

| Ingredients | Concentration | Ingredient weight (grams) | Active ingredient weight (grams) |
|---|---|---|---|
| KETTLE CHARGE | | | |
| Deionized water | 100% | 160.00 | 160.00 |
| RHODAPEX AB20 | 29% | 1.01 | 0.29 |
| Ammonium persulfate | 100.00% | 0.26 | 0.26 |
| MONOMER EMULSION | | | |
| Deionized water | 100% | 107.22 | |
| RHODAPEX AB20 | 29% | 1.01 | 0.29 |
| Methyl acrylic acid | | 29.20 | 29.20 |
| Ethyl acrylate | | 81.76 | 81.76 |
| Hydrophobic Monomer | 50.00% | 11.68 | 5.84 |
| MAEP or MAHP | 82.00% | 29.20 | |
| INITIATOR SOLUTION | | | |
| Deionized water | | 30.00 | 30.00 |
| Ammonium persulfate | | 0.37 | 0.37 |

TABLE 1-continued

| Ingredients | Concentration | Ingredient weight (grams) | Active ingredient weight (grams) |
|---|---|---|---|
| CHASER SOLUTION Part 1 | | | |
| Terbutyl peroxybenzoate | | 0.51 | 0.51 |
| Part 2 | | | |
| Isoascorbic acid (araboascorbic acid) | | 0.26 | 0.26 |
| Deionized water | | 8.76 | 8.76 |
| Total | | 461.24 | |
| Theoretical Solids | 30.1% | | |
| Scale-up factor | 1.46 | | |
| Seed | 2.0% ME | | 5.20 |
| | 25.0% IS | | 7.59 |

The HASE polymers are each made according to the following procedure. Add heat to kettle charge to about 80° C. while purging with $N_2$. Maintain $N_2$ blanket throughout run. At about 80° C., add 25% Initiator solution and 2% Monomer emulsion. Hold at that temperature for about 15 minutes. Feed remainder of monomer emulsion and initiator solution over 3 hours. Hold for 30 minutes, and add the chaser solution. Finally, heat to about 80° C. and hold for 30 minutes, and allow cooling.

In TABLE 1 RHODAPEX AB20 is a commercially available sulfated alcohol ethoxylate surfactant from Rhodia. Ammonium persulfate is an initiator. The initiator and chaser solutions are provided to convert left over monomers to oligomerize them to reduce VOCs. If desired to avoid the initiator and chaser solutions excess monomer could be removed by stripping. ME is an abbreviation for monomer emulsion. IS is an abbreviation for initiator solution.

MAEP is mono-[2-(methacryloyloxy)ethyl]phthalate. MAHP is mono-[2-(Methacryloyloxy)ethyl hexahydro]phthalate. These are embodiments of first acidic monomers.

Methyl acrylic acid is an embodiment of a second acidic monomer.

Ethyl acrylate is an embodiment of a nonionic, copolymerizable C2-C12 alpha, beta-ethylenically unsaturated monomer.

The hydrophobic monomer of Example 4 is a Nopol alkoxylate according to structure (VI):

(VI)

The Nopol alkoxylate is made as follows: Nopol is alkoxylated with propylene oxide and ethylene oxide charged to a glass flask equipped with a PTFE blade agitator, temperature sensor, dry compressed air purge line and a water cooled condenser. The liquid ethoxylate is warmed, stirred, and MEHQ is added. A purge of dry air is passed through the liquid and later methacrylic anhydride is added. The temperature is stabilized and held between 70-74° C. for five and a half hours, and then the liquid is cooled. Methacrylic acid and water are added and the liquid product is discharged.

TABLE 2A and TABLE 2B show results of latex characterization of HASE polymers as thickeners synthesized from ingredients generally in accordance with TABLE 1 such as MAEP or MAHP as a first acidic monomer, methyl acrylic acid as a second acidic monomer, ethyl acrylate as a nonionic, copolymerizable C2-C12 alpha, beta-ethylenically unsaturated monomer, and a hydrophobic monomer. However, the hydrophobic monomer is Hydrophobic Monomer 1 having formula VIa:

VIa

In TABLEs 2A and 2B Particle Size is average particle size. PDI is polydispersity index. ME is an abbreviation for monomer emulsion. Coagulum is % undesired solids.

TABLE 2A

Latex characterization of HASE thickeners synthesized from methyl acrylic acid, ethyl acrylate, Hydrophobic Monomer 1, and MAEP

| HASE Polymer | Z-Average Particle Size | PDI | % Coagulum | % Solids Content |
|---|---|---|---|---|
| 1[a] | 164.2 | 0.014 | 0.0698 | 30.66 |
| 2[b] | 123.9 | 0.019 | 0.109 | 31.65 |
| 3[c] | 156.1 | 0.019 | 0.202 | 32.09 |
| 4[d] | 173.1 | 0.012 | 0.102 | 31.52 |
| 5[e] | 131.9 | 0.04 | 0.0891 | 33.52 |
| 6[f] | 124 | 0.047 | 0.161 | 33.04 |
| 7[g] | 137 | 0.029 | 0.256 | 33.98 |

[a]Polymer synthesized using 1:0 MAEP/MAA ratio
[b]Polymer synthesized using 1:1 MAEP/MAA ratio
[c]Polymer synthesized using 1:3 MAEP/MAA ratio
[d]Polymer synthesized using 1:9 MAEP/MAA ratio
[e]Polymer synthesized using 1:1 MAEP/MAA ratio (less initiator added)
[f]Polymer synthesized using 1:1 MAEP/MAA ratio (more Hydrophobic Monomer 1 added)
[g]Polymer synthesized using 1:1 MAEP/MAA ratio (less initiator and more Hydrophobic Monomer 1 added)

TABLE 2B

Latex characterization of HASE Polymers 8-12 synthesized from methyl acrylic acid, ethyl acrylate, Hydrophobic Monomer 1, and MAEP or MAHP

| HASE Polymer | Z-average Particle Size | PDI | pH | % Coagulum | % Solids Content |
|---|---|---|---|---|---|
| 8[h] | 161.30 | 0.024 | 2.06 | 0.037 | 31.87 |
| 9[i] | 174.70 | 0.070 | 2.11 | 0.050 | 32.63 |
| 10[j] | 199.7 | 0.071 | 2.60 | 0.158 | 31.29 |
| 11[k] | 147.30 | 0.021 | 2.38 | 0.024 | 30.54 |
| 12[l] | 147.6 | 0.005 | 2.70 | 0.010 | 30.10 |

[h]Polymer synthesized using 1:1 MAEP/MAA ratio
[i]Polymer synthesized using 1:3 MAEP/MAA ratio
[j]Polymer synthesized using 0:1 MAEP/MAA ratio (control)
[k]Polymer synthesized using 1:0 MAEP/MAA ratio
[l]Polymer synthesized using 1:0 MAHP/MAA ratio Example 5

Sample Preparation for Thickening Efficiency (KU)

Formulation preparation combined 108 grams Binder latex (RHOPLEX SG30)+61 grams Deionized water+HASE polymer as a thickener. The binder latex RHOPLEX SG30 is an acrylic emulsion available from the Dow Chemical Company.

TABLES 3A and 3B show thickening efficiency in RHOPLEX SG30.

TABLE 3A lists Examples A-F which employed HASE Polymers 2-7 of TABLE 2A above.

TABLE 3B lists Examples G-K which employed HASE Polymers 8-12 of TABLE 2B above.

The HASE polymer was added as a thickener until a KU viscosity of 95+/−2 and pH=9-9.3 was reached.

TABLE 3A

Thickening Efficiency of HASE Polymer in RHOPLEX SG30 Acrylic Emulsion

| Binder and HASE Polymer System | HASE Polymer | Efficiency (g) | pH | KU Visc. (KU) | ICI Visc. (P) | BV (LV 4 @ 60 RPM) |
|---|---|---|---|---|---|---|
| A | 2[a] | 3.55 | 9.02 | 93.5 | 2.2 | 3249 |
| B[b] | 3[b] | 3.3 | 9.174 | 95.7 | 1.6 | 3439 |
| C | 4[c] | 3.16 | 9.462 | 96.4 | 0.50 | 3339 |
| D | 5[d] | 3.14 | 9.28 | 94.2 | 0.80 | 3759 |
| E | 6[e] | 3.78 | 9.004 | 95.4 | 0.6 | 3959 |
| F | 7[f] | 31.0 | 9.255 | 93.2 | 0.60 | 4209 |

[a]Polymer synthesized using 3:1 MAEP/MAA ratio
[b]Polymer synthesized using 1:3 MAEP/MAA ratio
[c]Polymer synthesized using 1:9 MAEP/MAA ratio
[d]Polymer synthesized using 1:1 MAEP/MAA ratio (less initiator added)
[e]Polymer synthesized using 1:1 MAEP/MAA ratio
[f]Polymer synthesized using 1:1 MAEP/MAA ratio (less initiator and more Hydrophobic Monomer 1 added)

TABLE 3B

Thickening Efficiency of HASE Polymer in RHOPLEX SG30 Acrylic Emulsion

| Binder and HASE Polymer System | HASE Polymer | Efficiency (g) | pH | KU Visc. (KU) | ICI Visc. (P) | BV (LV 4 @ 60 RPM) |
|---|---|---|---|---|---|---|
| G | 8[h] | 3.71 | 9.02 | 93.2 | 0.40 | 3359 |
| H | 9[i] | 3.04 | 9.05 | 95.3 | 0.40 | 3299 |
| I | 10[j] | 2.77 | 9.25 | 96.4 | 0.50 | 3339 |
| J | 11[k] | 21.47 | 9.15 | 94.2 | 0.80 | 3759 |
| K | 12[l] | 31.0 | 9.16 | 93.5 | 0.60 | 4209 |

[h]Polymer synthesized using 1:1 MAEP/MAA ratio
[i]Polymer synthesized using 1:3 MAEP/MAA ratio
[j]Polymer synthesized using 0:1 MAEP/MAA ratio (control)
[k]Polymer synthesized using 1:0 MAEP/MAA ratio
[l]Polymer synthesized using 1:0 MAHP/MAA ratio FIG. 1 shows Viscosity Profiles of Formulations prepared with HASE thickeners containing EGMHPT and MEPHM (in RHOPLEX SG30).

Figure 2:
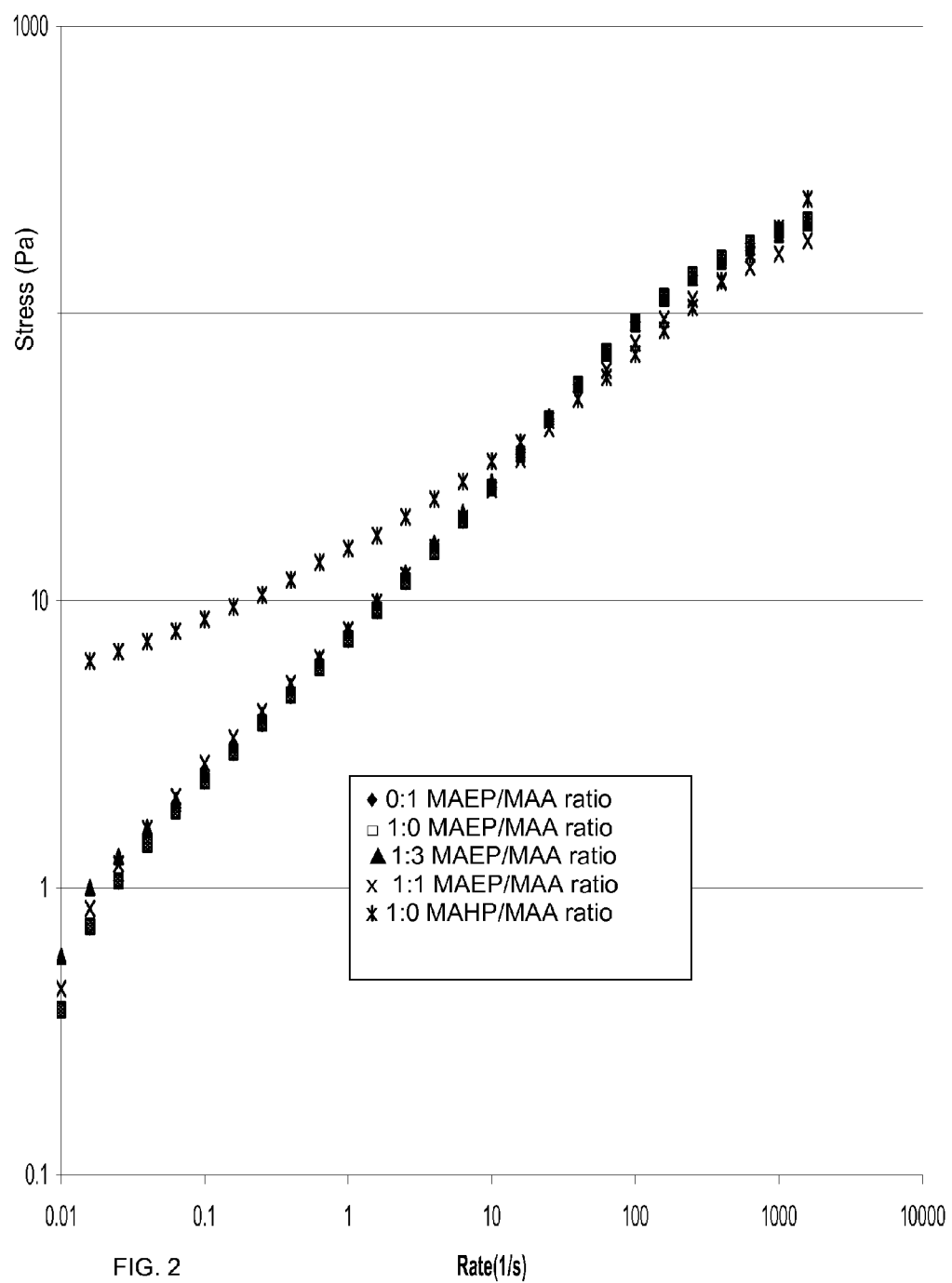
FIG. 2 shows Yield Stress of formulations prepared with HASE thickeners containing MAEP and MAHP (in RHOPLEX SG30).

FIG. 2 show Yield Stresses of Formulations prepared with HASE thickeners containing MAEP and MAHP (in RHOPLEX SG30).

Figure 3:
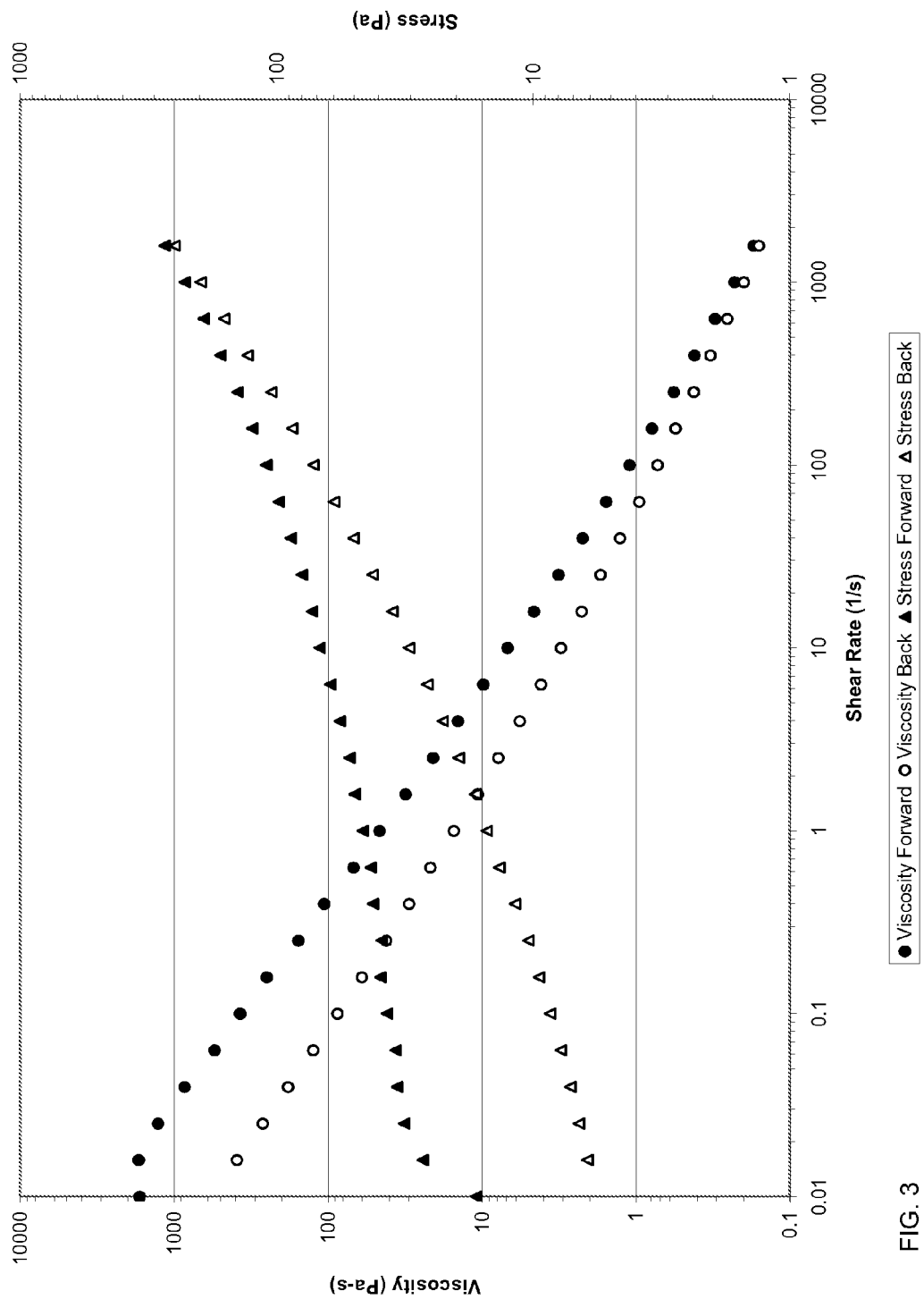
FIG. 3 shows thixotropic measurement of Binder and HASE Polymer System K of HASE polymer 12 in RHOPLEX SG30 (couette).

FIG. 3 shows thixotropic measurement of Binder and HASE Polymer System K of HASE polymer 12 in RHOPLEX SG30 (couette). In this example: Temperature was 25.0 degrees C. Couette flow refers to the laminar flow of a viscous fluid in the space between a bob and cup, one of which is moving relative to the other.

Figure 4:
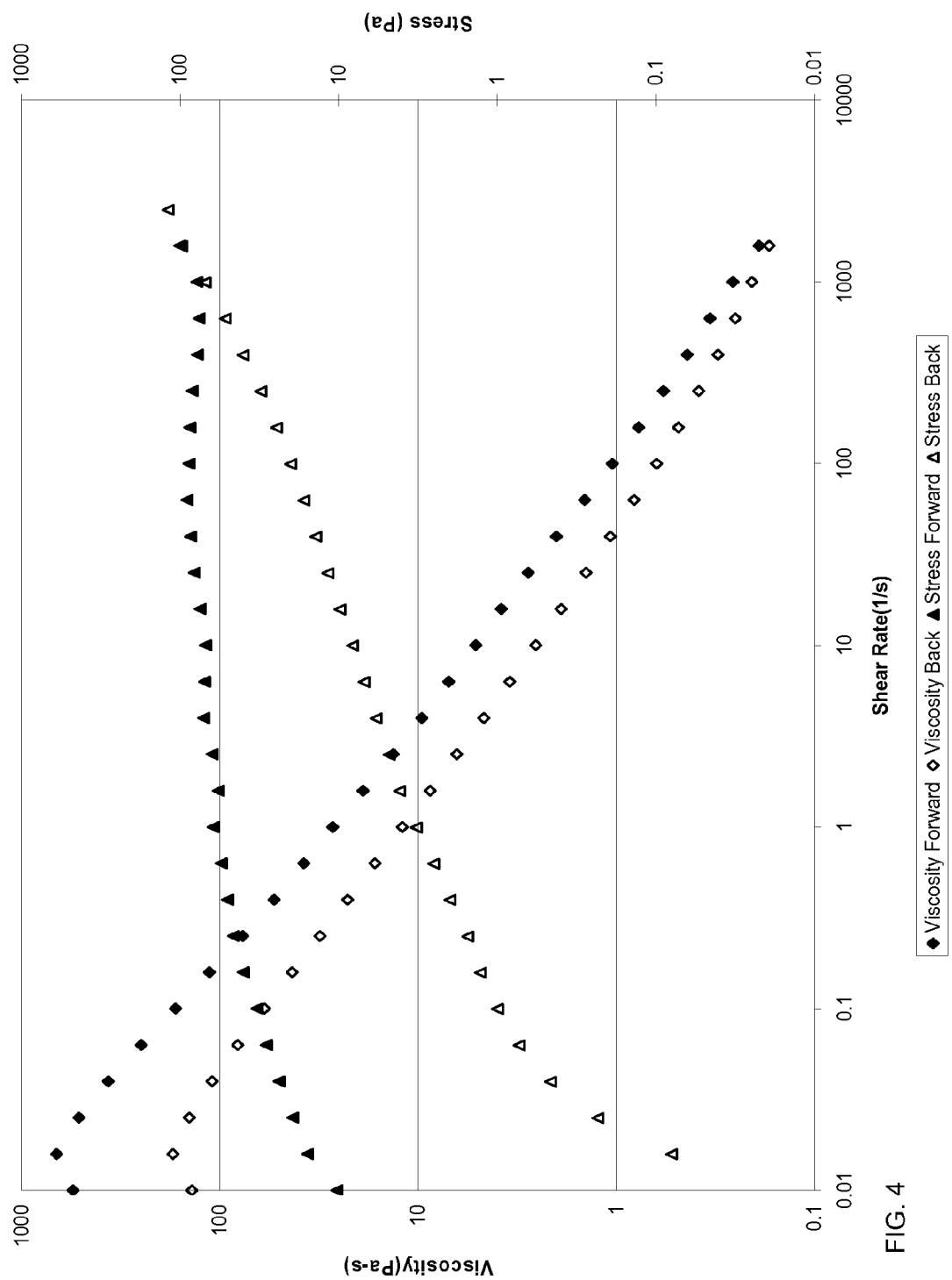
FIG. 4 shows the measurement of Binder and HASE Polymer System J of HASE polymer 11 in RHOPLEX SG30 (couette).

FIG. 4 shows the measurement of Binder and HASE Polymer System J of HASE polymer 11 in RHOPLEX SG30 (couette). In this example Temperature was 25.0 degrees C.

The data shows HASE thickeners incorporating MAEP and Methacrylic Acid (MAA) show good thickening efficiency.

It should be apparent embodiments other than those expressly described above come within the spirit and scope of the present invention. Thus, the present invention is not defined by the above description but by the claims appended hereto.

That which is claimed:

1. A HASE pH responsive copolymer of unsaturated copolymerizable monomers which is a water soluble thickener, said unsaturated copolymerizable monomers consisting of, based on total weight of monomers:

A. about 10-70 weight percent first acidic monomer selected from at least one member of the group consisting of mono-[2-(methacryloyloxy)ethyl]phthalate having the structure A.I:

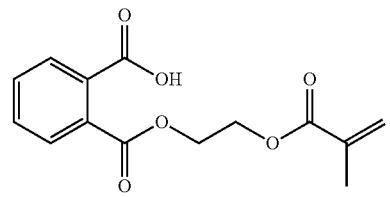

A.I and mono-[2-(Methacryloyloxy)ethyl hexahydro]phthalate having the structure A.II

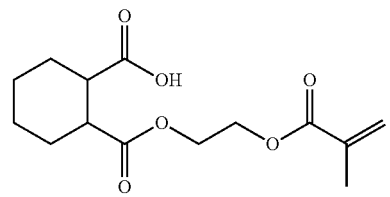

A.II

B. about 0-45 weight percent of at least one C3-C8 alpha beta-ethylenically unsaturated second acidic monomer;
C. about 15-70 weight percent of at least one nonionic, copolymerizable C2-C12 alpha, beta-ethylenically unsaturated monomer; and
D. about 0.05 to 30 weight percent of at least one nonionic ethylenically unsaturated hydrophobic monomer, wherein the hydrophobic monomer comprises one or more compounds according to structure (D.XXV):

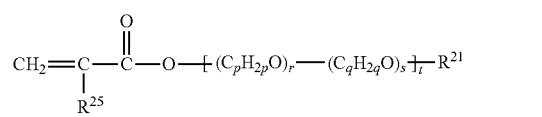

(D.XXV)

wherein
$R^{21}$ is linear $C_5$-$C_{50}$ alkyl, hydroxyalkyl, alkoxyalkyl, aryl, or arylalkyl,
$R^{25}$ is methyl or ethyl, and
p is 2,
q is 2 to 5,
r is an integer of from 1 to about 80,
s is 0
t is 1.

2. The pH responsive copolymer of claim 1, consists of, based on total weight of monomers:

A. about 10-70 weight percent first acid monomer selected from at least one member of the group consisting of mono-[2-(methacryloyloxy)ethyl]phthalate and mono-[2-(Methacryloyloxy)ethyl hexahydro]phthalate,
B. about 5 to 30 weight percent of at least one C3-C8 alpha beta-ethylenically unsaturated second acidic monomer;
C. about 15-70 weight percent of at least one non-ionic, copolymerizable C2-C12 alpha, beta-ethylenically unsaturated monomer; and D. about 0.05 to 30 weight percent at least one nonionic ethylenically unsaturated hydrophobic monomer.

3. The copolymer of claim 1, wherein the first acidic monomer is mono-[2-(methacryloyloxy)ethyl]phthalate.

4. The copolymer of claim 1, wherein the first acidic monomer is mono-[2-(methacryloyloxy)ethyl hexahydro]phthalate.

5. The copolymer of claim 1, wherein the carboxylic acid monomer is present from about 25 weight percent to about 60 weight percent based on total monomer weight.

6. The copolymer of claim 1, wherein the second acidic monomer is selected from a group consisting of methacrylic acid, acrylic acid and a combination thereof.

7. The copolymer of claim 1, wherein the nonionic, copolymerizable C2-C12 alpha, beta-ethylenically unsaturated monomer is alkyl acrylate.

8. An aqueous composition, comprising water and the pH responsive copolymer of claim 1.

9. The aqueous composition of claim 8, further comprising an emulsifier, wherein the aqueous composition is a pH responsive composition.

10. The aqueous composition of claim 9, having an average particle size of about 500 to about 3000 angstroms and a Brookfield viscosity of about 100 to about 500,000, cps as a 1 percent aqueous solution in ammonium salt at pH 9.0 and 25 degrees C.

11. The aqueous composition of claim 8, wherein the composition comprises, based on 100 parts by weight of the composition, from about 0.05 parts by weight to about 20 parts by weight of the pH responsive polymer.

12. The aqueous composition of claim 8, wherein the composition is an emulsion comprising an effective amount of the pH responsive compound, and further comprises an emulsifier and a film forming polymer latex, wherein the pH responsive copolymer is present in an amount effective for modifying the rheological properties of the emulsion.

13. The composition of claim 10, further comprising one or more of a pigment, a filler, or an extender.

14. The aqueous composition of claim 12, wherein the emulsion is selected from the group consisting of a latex paint, a latex coating, a cosmetic, a detergent/cleanser, and an oilfield drilling fluid.

15. The aqueous composition of claim 14, wherein the emulsion is a latex paint, further comprising at least one additive selected from the group consisting of dispersants, surfactants, rheology modifiers, defoamers, thickeners, biocides, mildewcides, colorants, waxes, perfumes and co-solvents to a mixture comprising the latex polymer and water.

16. The aqueous composition of claim 8, wherein the composition is a personal care composition and further comprises one or more surfactants and a personal care benefit agent.

17. The aqueous composition of claim 16, wherein the one or more surfactants comprise at least one anionic surfactant and the composition further comprises a structuring agent for the anionic surfactant.

18. The aqueous composition of claim 8, wherein the composition is a particle dispersion and further comprises particles dispersed in the composition.

19. A method for handling particles, comprising dispersing the particles in a composition according to claim 18, to form an aqueous particle dispersion.

20. The method of claim 19, further comprising transporting the aqueous particle dispersion by pumping the aqueous particle dispersion through a conduit.

21. The aqueous composition of claim 8, wherein the composition is a hydraulic fracturing composition and further comprises a proppant.

22. A method for fracturing a geologic formation, comprising directing a stream of the composition of claim 21 at a surface of the formation at a pressure and flow rate at least sufficient to initiate, extend, or initiate and extend one or more fractures in the formation.

23. A method for thickening an aqueous emulsion, comprising: forming a blend by blending with the aqueous emulsion an amount of the pH-responsive composition of claim 6 effective to thicken the aqueous emulsion when pH of the blend is adjusted to a pH in the range of about 6.5 to about 11.

24. A method for promoting personal care comprising applying the copolymer of claim 1 to skin or hair of a user.

25. A home care or industrial cleaning composition for cleaning fabrics or hard surfaces comprising, the copolymer of claim 1 and a surfactant and a home care or industrial cleaner benefit agent.

26. A method for cleaning a substrate selected from the group consisting of a hard surface and a fabric, comprising applying the composition of claim 25 to the substrate.

27. The copolymer of claim 1, wherein the copolymer comprises the hydrophobic monomer, wherein the hydrophobic monomeric units each independently comprise, per monomeric unit, at least one group according to structure (D.XXI):

wherein:
$R^{21}$ is $C_5$-$C_{50}$ linear alkyl, hydroxyalkyl, alkoxyalkyl, aryl, or aryalkyl,
$R^{22}$ is a bivalent polyether group,
$R^{23}$ is absent or is a bivalent linking group.

28. The copolymer of claim 1, wherein the at least one nonionic, copolymerizable C2-C12 alpha, beta-ethylenically unsaturated monomer is selected from one or more compounds according to the structure (C.III):

wherein:
$R^{41}$ is alkyl, hydroxyalkyl, alkoxyalkyl, cycloalkyl, aryl, aryalkyl, or aryloxy, and
$R^{42}$ is absent or is a bivalent linking group, and
$R^{43}$ is a moiety having a site of ethylenic unsaturation according to structure (C.IV):

wherein $R^{19}$ is H or $(C_1$-$C_4)$alkyl.

29. A HASE pH responsive copolymer of unsaturated copolymerizable monomers which is a water soluble thickener, said unsaturated copolymerizable monomers consisting of, based on total weight of monomers:
A. about 10-70 weight percent first acidic monomer selected from at least one member of the group consisting of mono-[2-(methacryloyloxy)ethyl]phthalate having the structure A.I:

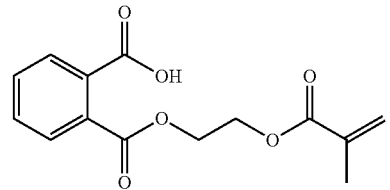

and mono-[2-(Methacryloyloxy)ethyl hexahydro]phthalate having the structure A.II

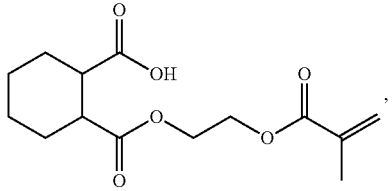

B. about 0-45 weight percent of at least one C3-C8 alpha beta-ethylenically unsaturated second acidic monomer, wherein the second acidic monomer is selected from a group consisting of methacrylic acid, acrylic acid and a combination thereof;

C. about 15-70 weight percent of at least one nonionic, copolymerizable unsaturated monomer, wherein the nonionic, copolymerizable unsaturated monomer is an alkyl acrylate according to structure (C.III):

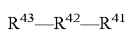 (C.III)

wherein:
$R^{41}$ is C1-C22 alkyl, and
$R^{42}$ is absent or is a bivalent linking group, and
$R^{43}$ is a moiety having a site of ethylenic unsaturation according to structure (C.IV):

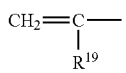 (C.IV)

wherein $R^{19}$ is H or $(C_1$-$C_4)$alkyl; and

D. about 0.05 to 30 weight percent of at least one nonionic ethylenically unsaturated hydrophobic monomer, wherein the hydrophobic monomer comprises one or more compounds according to structure (D.XXV):

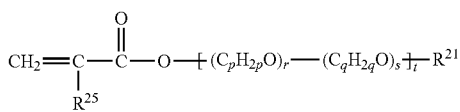 (D.XXV)

wherein
$R^{21}$ is $C_5$-$C_{50}$ alkyl, hydroxyalkyl, alkoxyalkyl, aryl, or arylalkyl,
$R^{25}$ is methyl or ethyl, and
p is 2, q is 2 to 5,
r is an integer of from 1 to about 80,
s is 0,
t is 1.

30. The pH responsive copolymer of claim 29, comprising about 5-45 weight percent of said at least one C3-C8 alpha beta-ethylenically unsaturated second acidic monomer.

31. The pH responsive copolymer of claim 30,
A. wherein the first acidic monomer is selected from at least one member of the group consisting of mono-[2-(methacryloyloxy)ethyl]phthalate and mono-[2-(Methacryloyloxy)ethyl hexahydro]phthalate, B. wherein the second acidic monomer is selected from a group consisting of methacrylic acid, acrylic acid and a combination thereof;
C. wherein $R^{41}$ of the alkyl acrylate is C1-C12 alkyl; and
D. wherein $R^{21}$ of the hydrophobic monomer is $C_5$-$C_{50}$ alkyl.

32. The pH responsive copolymer of claim 31, wherein the alkyl acrylate is selected from the group consisting of ethyl acrylate and ethyl methacrylate; and the hydrophobic monomer is

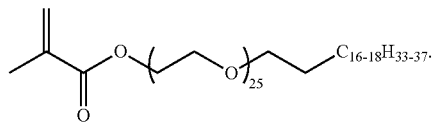

33. An ASE pH responsive copolymer of unsaturated copolymerizable monomers which is a water soluble thickener, said unsaturated copolymerizable monomers consisting of, based on total weight of monomers:

A. about 10-70 weight percent first acidic monomer selected from at least one member of the group consisting of mono-[2-(methacryloyloxy)ethyl]phthalate having the structure A.I:

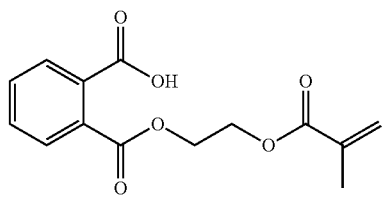

and mono-[2-(Methacryloyloxy)ethyl hexahydro]phthalate having the structure A.II

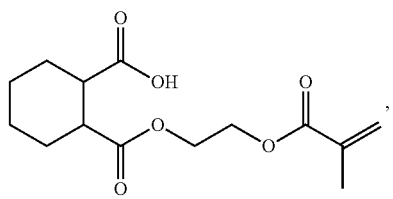

B. about 0-45 weight percent of at least one C3-C8 alpha beta-ethylenically unsaturated second acidic monomer, wherein the second acidic monomer is selected from a group consisting of methacrylic acid, acrylic acid and a combination thereof;
C. about 15-70 weight percent of at least one nonionic, copolymerizable unsaturated monomer, wherein the nonionic, copolymerizable unsaturated monomer is an alkyl acrylate according to structure (C.III):

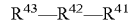 (C.III)

wherein:
$R^{41}$ is C1-C22 alkyl, and
$R^{42}$ is absent or is a bivalent linking group, and $R^{43}$ is a moiety having a site of ethylenic unsaturation according to structure (C.IV):

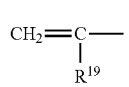   (C.IV)

wherein $R^{19}$ is H or $(C_1\text{-}C_4)$alkyl.

34. The pH responsive copolymer of claim 33, comprising about 5-45 weight percent of at least one C3-C8 alpha beta-ethylenically unsaturated second acidic monomer.

35. The pH responsive copolymer of claim 34,
  A. wherein the first acidic monomer is selected from at least one member of the group consisting of mono-[2-(methacryloyloxy)ethyl]phthalate and mono-[2-(Methacryloyloxy)ethyl hexahydro]phthalate,
  B. wherein the second acidic monomer is selected from a group consisting of methacrylic acid, acrylic acid and a combination thereof;
  C. wherein $R^{41}$ of the alkyl acrylate is C1-C12 alkyl.

36. The pH responsive copolymer of claim 35, wherein the alkyl acrylate is selected from the group consisting of ethyl acrylate and ethyl methacrylate.

* * * * *